(12) United States Patent
Fehlings et al.

(10) Patent No.: US 11,859,206 B2
(45) Date of Patent: Jan. 2, 2024

(54) GENERATION OF OLIGODENDROGENIC NEURAL PROGENITOR CELLS

(71) Applicant: UNIVERSITY HEALTH NETWORK, Toronto (CA)

(72) Inventors: Michael George Fehlings, Toronto (CA); Mohamad Khazaei, Toronto (CA)

(73) Assignee: University Health Network, Toronto (CA)

( * ) Notice: Subject to any disclaimer, the term of this patent is extended or adjusted under 35 U.S.C. 154(b) by 874 days.

(21) Appl. No.: 16/636,153

(22) PCT Filed: Jul. 30, 2018

(86) PCT No.: PCT/CA2018/050926
§ 371 (c)(1),
(2) Date: Feb. 3, 2020

(87) PCT Pub. No.: WO2019/023793
PCT Pub. Date: Feb. 7, 2019

(65) Prior Publication Data
US 2021/0024888 A1  Jan. 28, 2021

Related U.S. Application Data

(60) Provisional application No. 62/541,477, filed on Aug. 4, 2017.

(51) Int. Cl.
*C12N 5/079* (2010.01)
*C12N 5/00* (2006.01)
*C12N 5/0735* (2010.01)

(52) U.S. Cl.
CPC .......... *C12N 5/0622* (2013.01); *C12N 5/0018* (2013.01); *C12N 5/0068* (2013.01); *C12N 5/0606* (2013.01); *C12N 2501/11* (2013.01); *C12N 2501/115* (2013.01); *C12N 2501/135* (2013.01); *C12N 2501/602* (2013.01)

(58) Field of Classification Search
CPC .. C12N 5/0622; C12N 5/0068; C12N 5/0018; C12N 5/0606; C12N 2501/11; C12N 2501/115; C12N 2501/135
USPC ........................................ 435/368, 377, 405
See application file for complete search history.

(56) References Cited

U.S. PATENT DOCUMENTS

2004/0009593 A1* 1/2004 Keirstead ................ A61P 25/00
435/368
2015/0011579 A1   1/2015 Sanofi

FOREIGN PATENT DOCUMENTS

WO       2015179822 A1   11/2015

OTHER PUBLICATIONS

Gorris, et al. "Pluripotent Stem Cell-Derived Radial Glia-Like as Stable Intermediate for Efficient Generation of Human Oligodendrocytes". Glia. 2015. (63):12. 2152-67 (Year: 2015).*
Gorris et al., "Pluripotent stem cell-derived radial glia-like cells as stable intermediate for efficient generation of human oligodendrocytes". Glia. Dec. 2015; 63(12): 2152-2167 (Year: 2015).*
Ahuja, C. S., et. al. Concise review: Bridging the gap: Novel neuroregenerative and neuroprotective strategies in spinal cord injury. Stem Cells Translational Medicine, 2016, 5, 914-924.
Ahuja, C., et. al. Recent advances in managing a spinal cord injury secondary to trauma [version 1; referees: 2 approved]. F1000Research, 2016, 5(F1000 Faculty Rev):1017.
Barres, B. A., et. al. A novel role for thyroid hormone, glucocorticoids and retinoic acid in timing oligodendrocyte development. Development, 1994, 120, 1097-1108.
Chambers, S. M., et. al. Highly efficient neural conversion of human ES and iPS cells by dual inhibition of SMAD signaling. Nature Biotechnology, 2009, 27, 275-280.
Chang D.J., et. al. Contralaterally transplanted human embryonic stem cell-derived neural precursor cells (ENStem-A) migrate and improve brain functions in strokedamaged rats. Experimental & Molecular Medicine, 2013, 45, e53.
Fehlings, M. G., et. al. The relationships among the severity of spinal cord injury, residual neurological function, axon counts, and counts of retrogradely labeled neurons after experimental spinal cord injury. Experimental Neurology, 1995, 132, 220-228.
Ghasemi-Dehkordi P., et. al. Comparison between the cultures of human induced pluripotent stem cells (hiPSCs) on feeder-and serumfree system (Matrigel matrix), MEF and HDF feeder cell lines. Journal of Cell Communication and Signaling, 2015, 9, 233-246.
Hawryluk G. W., et. al. An examination of the mechanisms by which neural precursors augment recovery following spinal cord injury: A key role for remyelination. Cell Transplant, 2014, 23, 365-380.
Khazaei, M., et. al. Induced pluripotent stem cells for traumatic spinal cord injury. Frontiers in Cell and Developmental Biology, Jan. 2017, 4, 152.

(Continued)

*Primary Examiner* — Anne Marie S Wehbe
*Assistant Examiner* — Hanan Isam Abuzeineh
(74) *Attorney, Agent, or Firm* — Bereskin & Parr LLP; Carmela De Luca

(57) ABSTRACT

Provided herein are methods of producing, compositions comprising and uses of oligodendrogenic neural progenitor cells (o-NPCs), made using a combination of PDGFR agonist and thyroxin or a thyroxin analogue. The method includes; obtaining ventralized neural progenitor cells (NPCs), the ventralized NPCs expressing Sox2, Nkx6-1, decreased level of Pax6 compared to unpatterned NPCs, and elevated expression of HoxA4 compared to unpatterned NPCs; culturing the ventralized NPCs for about 12 to about 16 days (days 26-40 of FIG. 7; days 12 to 27 of FIG. 10) in neural expansion media (NEM) supplemented with i) PDGFR agonist for the about 12 to about 16 days and ii) thyroxine or a thyroxine analogue for the latter about 7 to about 9 days, to produce o-NPC expressing Sox2 and Nkx2.2, decreased level of Pax6 and Nkx6.1 compared to ventralized NPCs and elevated level of HoxA4 and Olig2 compared to ventralized NPCs.

20 Claims, 18 Drawing Sheets

(56) References Cited

OTHER PUBLICATIONS

Le Dreau, G., et. al. Dorsal-ventral patterning of the neural tube: A tale of three signals. Developmental Neurobiology, 2012, 72, 1471-1481.

Lu, Q. R., et. al. Common developmental requirement for olig function indicates a motor neuron/oligodendrocyte connection. Cell, 2002, 109, 75-86.

Papastefanaki, F., et. al. From demyelination to remyelination: The road toward therapies for spinal cord injury. Glia, 2015, 63, 1101-1125.

Plaisted W. C., et. al. Remyelination Is correlated with regulatory T cell induction following human embryoid body-derived neural precursor cell transplantation in a viral model of multiple sclerosis. PLoS One, 2016, 11, e0157620.

Skop, N. B., et. al. Optimizing a multifunctionalmicrosphere scaffold to improve neural precursor cell transplantation for traumatic brain injury repair. Journal of Tissue Engineering and Regenerative Medicine, 2016, 10, E419-E432.

Takahashi, K., et. al. Induction of pluripotent stem cells from mouse embryonic and adult fibroblast cultures by defined factors. Cell, 2006, 126, 663-676.

Wang S., et. al. Human iPSC-derived oligodendrocyte progenitor cells can myelinate and rescue a mouse model of congenital hypomyelination. Cell Stem Cell, 2013, 12, 252-264.

Wilson, L., et. al. The mechanisms of dorsoventral patterning in the vertebrate neural tube. Developmental Biology, 2005, 282, 1-13.

Zhou, Q., et. al. The bHLH Transcription factor Olig2 promotes oligodendrocyte differentiation in collaboration with Nkx2.2. Neuron, 2001, 31, 791-807.

Zweckberger, K., et. al. Self-assembling peptides optimize the post-traumatic milieu and synergistically enhance the effects of neural stem cell therapy after cervical spinal cord injury. Acta Biomaterialia, 2016, 42, 77-89.

Sundberg, M., et. al. Production and isolation of NG2+ oligodendrocyte precursors from human embryonic stem cells in defined serum-free medium. Stem Cell Research, 2010, vol. 5, 91-103.

Gorris, R., et. al. Pluripotent Stem Cell-Derived Radial Glia-Like Cells as Stable Intermediate for Efficient Generation of Human Oligodendrocytes. Glia, 2015, vol. 63, 2152-67.

Khazaei, M., et. al. Generation of Oligodendrogenic Spinal Neural Progenitor Cells From Human Induced Pluripotent Stem Cells. Current Protocols in Stem Cell Biology, 2017, vol. 42, 2D.20.1-2D.20.14.

Khazaei, M., et. al. Directly reprogrammed neural precursor cells—a novel source for cell replacement therapy in spinal cord injury. Poster. ISSCR Anual Meeting, Boston, Jun. 14, 2017.

Khazaei, M., et. al. Directly reprogrammed human neural precursor cells: a novel population of cells that promote repair and functional recovery following spinal cord injury. Abstract. ISSCR Anual Meeting, Boston, Jun. 14, 2017.

S.A. Goldman et al. Flow to make an oligodendrocyte. Development. vol. 142, No. 23, Dec. 1, 2015, pp. 3983-3995.

* cited by examiner

Caudalization and Ventralization of hiPSC-NPCs

Differentiation of hiPSC-NPCs to oligodendrogenic fate

A

B

C

D

E

F

A

GENERATION OF OLIGODENDROGENIC NEURAL PROGENITOR CELLS

CROSS-REFERENCE TO RELATED APPLICATIONS

This application is a national phase entry of PCT/CA2018/050926, filed Jul. 30, 2018, which claims priority from Canadian patent application number 3,006,897, filed Jun. 1, 2018, and U.S. Provisional patent application serial number 62/541,477 filed Aug. 4, 2017; each of these applications being incorporated herein in their entirety by reference.

FIELD

The disclosure relates to methods and compositions for the generation of oligodendrogenic neural progenitor cells (o-NPCs) from human induced pluripotent stem cells (hiPSCs).

BACKGROUND

Transplantation of human induced pluripotent stem cell-derived neural precursor cells (hiPS-NPCs) represents an exciting approach to regenerate the central nervous system (CNS) after insult such as trauma, e.g., traumatic brain injury; traumatic spinal cord injury (SCI); autoimmune disease, e.g., multiple sclerosis (MS); amyotrophic lateral sclerosis; degeneration, e.g., Alzheimer's disease or Parkinson's disease; and a plethora of other illnesses (Ahuja & Fehlings, 2016; Plaisted et al., 2016; Skop, Calderon, Cho, Gandhi, & Levison, 2016; Zweckberger, Ahuja, Liu, Wang, & Fehlings, 2016). However, the proportion of neurons, astrocytes, and oligodendrocytes required to repair and/or replace damaged cells is not known. In several conditions, such as SCI and MS, it is clear that chronic demyelination of long-tract axons plays an important role in producing neurological deficits (Fehlings & Tator, 1995). In these instances, tripotent hiPS-NPCs, which have the ability to differentiate into oligodendrocytes, neurons, and astrocytes remain a viable strategy, however, it may be desirable to bias differentiation towards an oligodendrocyte lineage to enhance regeneration of myelin and promote sensorimotor recovery (Ahuja, Martin, & Fehlings, 2016; Hawryluk et al., 2014; Papastefanaki & Matsas, 2015).

Goldman published a method for generating oligodendrocyte precursor cells (OPCs) from human iPSCs that takes about 160 days (Wang et al., 2013).

SUMMARY

An aspect of the disclosure includes a method of producing oligodendrogenic neural progenitor cells (o-NPCs), the method comprising:
  a) obtaining ventralized neural progenitor cells (NPCs), the ventralized NPCs expressing Sox2, Nkx6-1, decreased level of Pax6 compared to unpatterned NPCs, and elevated expression of HoxA4 compared to unpatterned NPCs;
  b) culturing the ventralized NPCs for about 12 to about 16 days (days 26-40 of FIG. 7; days 12 to 27 of FIG. 10) in neural expansion media (NEM) supplemented with i) PDGFR agonist for the about 12 to about 16 days and ii) thyroxine or a thyroxine analogue for the latter about 7 to about 9 days, to produce o-NPC expressing Sox2 and Nkx2.2, decreased level of Pax6 and Nkx6.1 compared to ventralized NPCs and elevated level of HoxA4 and Olig2 compared to ventralized NPCs.

In an embodiment, the NEM of steps b) i) and ii) is also supplemented with an FGF receptor (FGFR agonist), optionally FGF2.

In an embodiment, the o-NPCs produced are biased to differentiation towards oligodendrocytes, and optionally produce at least 30% oligodendrocytes when differentiated.

In an embodiment, the ventralized NPCs are obtained from unpatterned NPCs, optionally by culturing unpatterned NPCs expressing Sox2+, Pax6+ and Otx2+ for about 12 days in NEM supplemented with i) retinoic acid and/or a retinoic acid analogue, optionally synthetic retinoid EC23 for the preliminary about 7 to 11 days, optionally about 9 days, and ii) a sonic hedgehog (Shh) agonist for the latter about 6 to about 12 days or until Otx2 expression is lost or decreased by at least 3 folds (log 2 scale) and/or HoxA4 expression is gained or increased by at least 3 folds (log 2 scale) compared to the unpatterned NPCs.

In an embodiment, the Ssh agonist is selected from purmorphamine, smoothened agonist (SAG) and recombinant Shh polypeptide.

In an embodiment, the unpatterned NPCs are cultured in NEM supplemented with EGF for the preliminary about 7 to 11 days of the about 12 day culture and cultured in NEM supplemented with FGFR agonist, optionally FGF2 and lacking RA receptor (RAR) agonist, such as RA for a latter about 3 days of the about 12 day culture.

In an embodiment, the unpatterned NPCs are obtained by culturing columnar cells that are in the form of rosettes and which express Pax6, in NIM supplemented with EGF receptor (EGFR) agonist, optionally EGF or betacelluin.

In an embodiment, the columnar cells that are in the form of rosettes are obtained by culturing iPSCs in neural induction media (NIM) for about 8 to about 10 days.

In an embodiment, wherein one or more of the culturing steps are cultured using a monolayer system.

In an embodiment, the columnar cells are cultured in a vessel coated with a gelatinous matrix.

Also provided in another aspect is a method of producing o-NPCs, the method comprising:
  a) obtaining iPSCs cultured for at least about 2 days in vessels comprising a gelatinous matrix with an induced pluripotent cell media/embryonic cell media supplemented with a ROCK inhibitor culturing the iPSCs:
  b) in NIM supplemented with leukemia inhibitory factor (LIF), FGFR agonist, B27 supplement (or equivalent) lacking vitamin A, N2 supplement, TGFb inhibitor, BMP inhibitor, optionally Noggin, AMP-activated protein kinase (AMPK) inhibitor, optionally compound C or Dorsomorphin for about 7 days; and
  c) in NIM supplemented with EGFR agonist, FGFR agonist, B27 or equivalent lacking vitamin A and N2 supplement, wherein the iPSCs are cultured in vessels coated with a gelatinous matrix comprising poly-L-lysine/laminin for about 1 to 2 days to produce columnar cells in the form of rosettes expressing Pax 6;
  d) culturing the columnar cells in the form of rosettes from step b. in NEM comprising EGFR agonist, FGFR agonist, B27 supplement or equivalent lacking vitamin A and N2 supplement for about 4 days, wherein the iPSCs are cultured in vessels coated with a gelatinous matrix comprising poly-L-lysine/laminin, to produce unpatterned NPCs;
  e) culturing the unpatterned NPCs from step c) for about 6 days in NEM comprising retinoic acid, N2 supplement, B27 supplement or equivalent, EGF agonist and a Shh agonist to produce caudalized NPCs;

f) culturing the caudalized NPCs from step d):
g) in NEM comprising EGFR agonist, N2 supplement, B27 supplement or equivalent, RAR agonist, optionally retinoic acid and Shh agonist for about 3 days (days 20 to 23 of FIG. 6); and
h) in NEM comprising FGFR agonist, optionally FGF2, N2 supplement, B27 supplement or equivalent and a Shh agonist for about 3 days (days 23 to 26 of FIG. 6) to obtain ventralized NPCs;
i) culturing the ventralized NPCs for about 12 to about 16 days in NEM comprising i) PDGFR agonist for the about 12 to about 16 days; ii) B27 supplement or equivalent and N1 supplement for the preliminary about 12 days; and iii) thyroxine or a thyroxine analogue for the latter about 7 to about 9 days, to produce o-NPCs.

In an embodiment, the iPSCs are hiPSCs.

In an embodiment, the hiPSCs are a cell line.

In an embodiment, wherein the thyroxine analogue is selected from thyroxine, levothyroxine sodium hydrate and triiodothyronine/thyroid hormone 3 (T3).

A further aspect includes a tripotent cell population produced according to the method described herein comprising at least or about 50%, at least or about 60%, at least or about 70%, at least or about 80%, at least or 90%, optionally about 50% to about 95% or about 90% to about 95% o-NPCs based on immunocytochemical Olig2 staining and a carrier, optionally a pharmaceutically acceptable carrier.

In an embodiment, the o-NPCs have been passaged 2, 3, 4 5 or 6 passages.

In an embodiment, the method further comprises differentiating the oNPCs to obtain a differentiated population enriched for oligodendrocyte lineage cells, optionally Olig2+ immature and GST-pi+ mature oligodendrocytes.

In an embodiment, the step of differentiating the oNPCs comprises culturing oNPCs in NEM lacking FGFR agonist/EGFR agonist, optionally FGF2/EGF to produce a radial glial cell 3CB2 enriched population of cells.

In an embodiment, the oNPCs are on vessels coated with spinal cord homogenate, optionally injured or naïve spinal cord homogenate.

A cell population comprising oligodendrocytes produced according to the method described herein and a carrier, optionally a pharmaceutically acceptable carrier.

In an embodiment, the pharmaceutically acceptable carrier is a culture media, optionally GMP grade or sterile.

In an embodiment, the culture media is NEM.

A further aspect is use of a cell population of described herein to treat a subject with a spinal cord injury or demyelination disease.

In an embodiment, the spinal injury is a cervical or thoracic spinal cord injury, optionally acute or chronic.

In an embodiment, the demyelination disease is MS or CP.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments are described below in relation to the drawings in which.

DETAILED DESCRIPTION OF THE DISCLOSURE

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Most current protocols for differentiation of caudalized neural progenitor cells (also referred to as neural precursor cells) (NPCs) are based on knowledge of mouse and chicken spinal cord embryology. Although the embryologic origin of oligodendrogenic cells continues to be investigated, a general consensus exists that early stage oligodendrocyte precursor cells (OPCs) and motor neurons share a developmental lineage in the spinal cord. Goldman and colleagues have described a method for generating OPCs from hiPSCs, however, the greatest drawback of their protocol is the lengthy culture time requiring proportionally greater quantities of expensive growth factors (Wang et al., 2013).

Described herein are methods for generating a cell type biased to produce oligodendrocytes, herein referred to as o-NPCs. These cells are similar to conventional NPC in that they are tripotent but are different in that they produce different ratios of these cells when differentiated. The methods described herein such as the protocol described in Example 1 substantially reduces differentiation time making the generation of o-NPCs for research and therapy more feasible.

Figure 1:
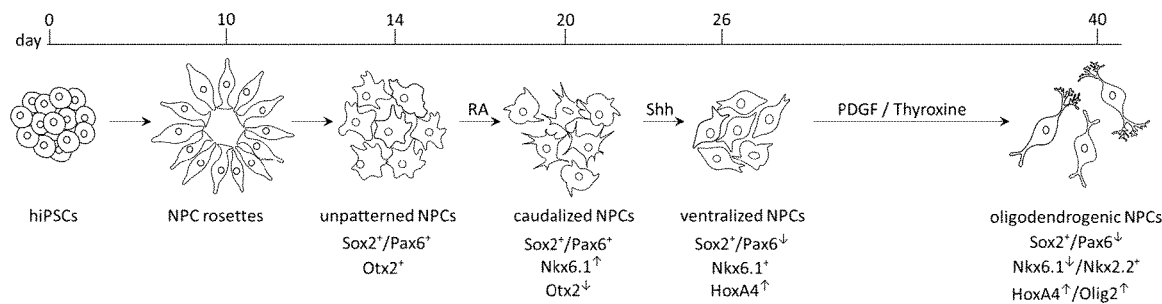
FIG. 1 Overview of the generation of o-NPCs from hiPSCs using this 40 day protocol. o-NPCs, oligodendrogenic neural progenitor cells; hiPSCs, human induced pluripotent stem cells.
Figure 3:
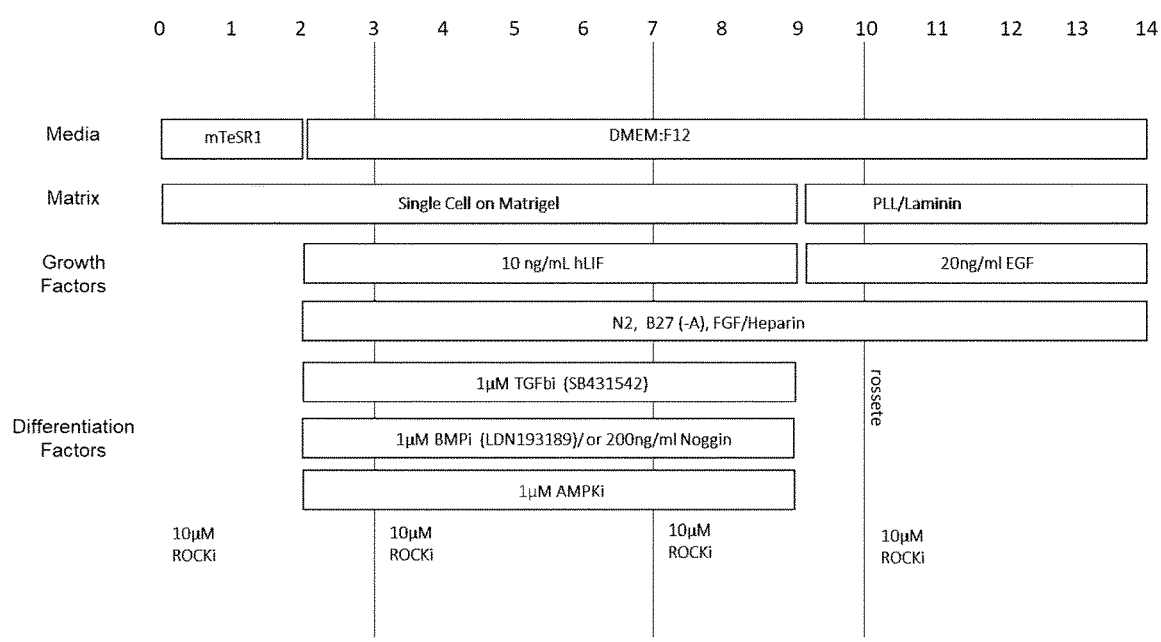
FIG. 3 Example of daily culture conditions for differentiation of NPCs from hiPSCs. Monolayer cells can be treated with dual SMAD inhibitors for 7-8 days. At the end of this step, neuro ectodermal rosettes emerge. Cells can be passaged every 3-4 days and replated at the density of 250,000 cells/cm$^2$. For the first 24 hr after each passage, cells can be supplemented with ROCK inhibitor. NPCs, neural progenitor cells; hiPSCs, human induced pluripotent stem cells.
Figure 6:
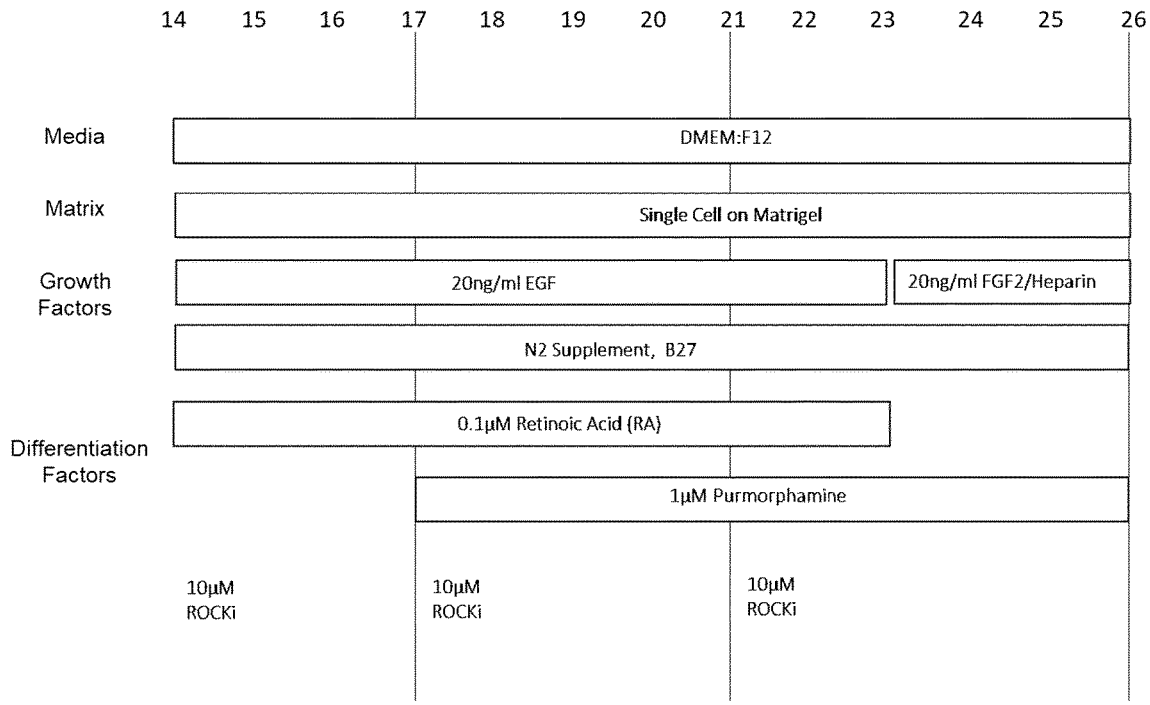
FIG. 6 Caudalization and ventralization of NPCs using RA and a Shh agonist (purmorphamine). NPCs, neural progenitor cells; RA, retinoic acid; Shh, sonic hedgehog.
Figure 7:
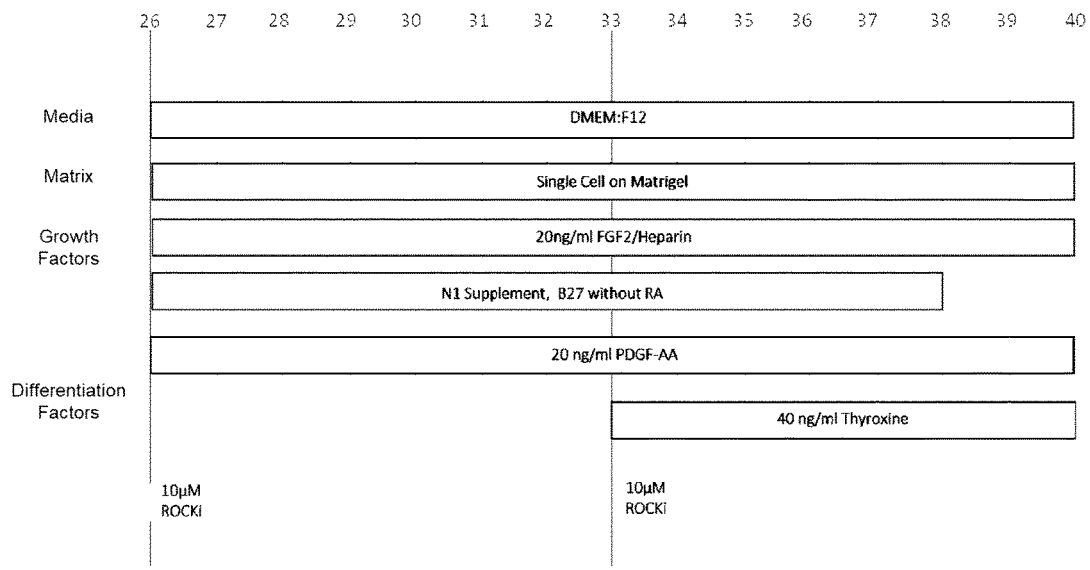
FIG. 7 Culture conditions from days 26 to 40; the last step for the generation of o-NPCs is supplementation with PDGF-AA and thyroxine. o-NPCs, oligodendrogenic neural progenitor cells.

The differentiation, isolation, and expansion protocols described herein for example as shown in FIGS. 3, 6 and 7 to generate o-NPCs from hiPSCs requires ~40 days. Different factors are added to different stages of differentiated hiPSCs according to an approximate timeline as described in FIG. 1. References to days generally correlates to the days identified in FIGS. 1, 3, 6 and 7. Also described are markers to characterize the cells at each stage for example as shown in FIG. 1.

Like conventional NPCs, o-NPCs generated using the present methods are tripotent cells and have the ability to differentiate into neurons, astrocytes, and oligodendrocytes, however, o-NPCs have a bias to differentiate predominantly into oligodendrocytes, both in vitro and in vivo. For example, the methods described herein have been found to increase oligodendrocyte production by at least 35%, at least 40%, at least 45%, at least 50%, at least 55%, at least 60% or at least 65% in vitro. Depending on the type of spinal cord injury, e.g. cervical, thoracic, chronic and/or acute, the methods described herein have been found to increase oligodendrocyte production by at least 35%, at least 40%, at least 45%, at least 50%, at least 55% or at least 60% compared to conventionally prepared NPCs.

Accordingly an aspect of the present disclosure includes a method of producing oligodendrogenic neural progenitor cells (o-NPCs), the method comprising:

a. obtaining ventralized neural progenitor cells (NPCs), the ventralized NPCs expressing Sox2 and NKx6.1 and decreased level of Pax6 compared to unpatterned NPCs and increased expression of HoxA4 compared of unpatterned NPCs.

b. culturing the ventralized NPCs for about 12 to about 16 days (days 26-40 of FIG. 7) in neural expansion media (NEM) supplemented with i) PDGF receptor (PDGFR) agonist for the about 12 to about 16 days; and ii) thyroxine or a thyroxine analog for the latter about 7 to about 9 days, to produce o-NPC expressing Sox2, Nkx2.2, decreased expression of Pax6 and Nkx6.1 compared to ventralized NPCs and increased expression of HoxA4 and Olig2 compared to ventralized NPCs.

The term "ventralized NPCs" as used herein refers to NPCs which express Sox2 and Nestin, have decreased expression of Pax6, FoxG1, Otx2 and Gbx2, and have increased expression of Nkx6.1, HoxA4, HoxB4 HoxC4 and HoxC5, all relative to un-patterned-NPCs. For example such cells can have at least 20% decreased expression of Pax6, at least 75% decreased level of expression for FoxG1, Otx2 and Gbx2, at least 50% increased expression Nkx6.1, and have at least 50% increased expression of HoxA4, HoxB4 HoxC4 and HoxC5, all relative to unpatterned-NPCs. Further, the expression level of Olig2 and Nkx2.2 is less than the expression of these genes compared to o-NPCs, for example ventralized NPCs typically express at least 25% less protein and at least about 2 fold or at least about 3 fold (Log 2 scale) less RNA, determined for example by density of immune staining and qRT-PCR respectively, than the expression level of these two genes compared to o-NPCs. Olig2 refers to oligodendrocyte transcription factor, Nkx2.2 and Nkx6.1 refer to homeobox proteins Nkx2.2 and Nkx6.1 and Sox2 also known as SRY (sex determining region Y)-box 2 which is a marker of neural stem progenitor cells (NSPCs). Sox2 along with Pax6 and Nestin are three main markers for NSPCs. Pax6 refers to paired box protein Pax6. HoxA4, HoxB4, HoxC4 and HoxC5 refer to homeobox proteins A4, B4, C4 and C5 respectively. FoxG1 refers to forkhead box protein G1. Otx2 and Gbx2 refer to homeobox proteins Otx2 and Gbx2 respectively.

The term "unpatterned NPCs" as used herein means directly reprogrammed NPCs that have not been caudalized and express Sox2/Pax6 and Otx2 (increased relative to NPC rosettes from which they can be derived). As shown in FIG. 1, they can be obtained at about 14 days using a protocol described herein. When the unpatterned NPCs are derived from hiPC cells they can be referred to as hiPS-derived unpatterned-NPCs hiPS-derived unpatterned-NPCs.

The term "NPCs" as used herein refers to neural progenitor cells, interchangeably referred to as neural precursor cells and neural stem cells (NPS). NPCs are tripotent cells with the potential to be differentiated to neurons, astrocytes and oligodendrocytes. NPC express Pax6, Sox2 and Nestin as the main NPC markers.

Any line of hiPSCs or hESCs can be used that will generate NPCs. Further any NPCs can be used. They can be derived form different methods (e.g. dual SMAD inhibition, directly reprogrammed, default pathway, embryoid body and etc) from hiPSC or hECS or NPCs derived from human fetal or adult tissue can be used as long as the NPCs are tripotent, e.g. have the potential to be differentiated to neurons, astrocytes and oligodendrocytes. Said cells should express Nestin, Sox2 and Pax6 and can have rostral identity (optional) (expressing Otx2 and/or FoxG1) or caudal identity (optional) (expressing any of the Hox genes such as HoxA4, and/or HoxB4 and/or Hox C4). Preferably they should not express any or detectable levels of HoxB9 and/or HB9.

The term "NEM" or "neural expansion media" as used herein means a base media suitable for culturing neural progenitor cells such as DMEM/F12, Neuralbasal Media etc comprising one or more of sodium pyruvate, a glutamine product such as glutamine or GlutaMAX™, one or more antibiotics such as penicillin and/or streptomycin, a supplement such as B27 supplement without vitamin A or equivalent (e.g. without RA or RA analogue) and depending on the stage of cell differentiation, one or more of an FGFR agonist such as FGF2, an EGFR agonist such as EGF and/or heparin. An example of a suitable NEM is provided in Example 1. Other suitable medias, supplements, antibiotics etc are known in the art and can be used. Typically the culture media will include non essential amino acids such as Glycine, L-Alanine, L-Asparagine, L-Aspartic acid, L-Glutamic Acid, L-Proline, L-Serine, glucose or equivalent, sodium pirovate, Catalase, Glutathione reduced, Insulin, Superoxide Dismutase, Holo-Transferin, Triiodothyronine (T3), L-carnitine, Ethanolamine, D+-galactose, Putrescine, Sodium selenite, Corticosterone, Linoleic acid, Linolenic acid, Progesterone, Retinol acetate, DL-alpha tocopherol (vit E), DL-alpha tocopherol acetate, Oleic acid, Pipecolic acid, Biotin to which FGF receptor agonist, optionally FGF2, EGFR agonist such as EGF or betacelluin, and optionally heparin are added.

The term "B27 supplement" as used herein refers to a serum free vitamin containing supplement that supports neurons and which is used with neuronal cell culture. Any such supplement that permits feeder layer independent growth can be used. B27 supplement includes for example Catalase, Glutathione, Insulin, Superoxide Dismutase, Human Holo-Transferin, T3, L-carnitine, Ethanolamine, D+-galactose, Putrescine, Sodium selenite, Corticosterone at, Linoleic acid, Linolenic acid, Progesterone at, Retinol acetate, DL-alpha tocopherol (vit E), DL-alpha tocopherol acetate, Oleic acid, Pipecolic acid-, and Biotin.

The period of PDGFR agonist incubation including the combined PDGFR agonist/thyroxine PDGFR agonist/thyroxine analogue incubation is approximately 12 to 16 days and this corresponds generally to days 24 to 40 as shown in FIG. 7. A person skilled in the art will recognize that the days of culture will depend on the culture conditions used including for example the exact differentiation status of the starting population.

The o-NPCs (also referred to as oNPCs) produced show for example 10-20% increased level of expression of HoxA4, and HoxB4, 30-40% increased level of expression of Olig2 and a 10-20% decreased level of expression of Pax6 and Nkx6.1 compared to ventralized-NPCs. These cells have spinal cord identity, meaning that the expression level of transcription factors which spatially are specific for spinal cord, like HoxA4, HoxB4, HoxC4 and HoxC5 which are for example at least 75% more than those in un-patterned NPCs, and do not express markers associated with brain identity cells. They are tripotent meaning that they have the potential to generate neurons, astrocytes and oligodendrocytes but are biased to differentiation towards for example at least 50% more oligodendrocytes compared to un-patterned NPCs.

o-NPCs, unlike un-patterned-NPCs, are caudalized, ventralized and are oligogenic. The different stages can for example be assessed by expression levels of one or more genes. For example, caudalized cells (compared to un-patterned cells) have elevated levels of HoxA4, B4, C4 and C5 (for example about around 50% more) but not as much as endpoint stage in o-NPCs which have increased levels that are about or at least 75% higher. Ventralized cells have a decrease in Pax6 expression (around 20-25%) and an increase in Nkx6.1 expression (around 25% or more) compared to to caudalized cells.

The term "PDGFR agonist" as used herein means any protein or small molecule that can activate the PDGF receptor A and/or PDGF receptor B (e.g. molecules that bind to PDFGR, induce the dimerization of the receptor and activate the signaling P13K pathway and STAT1/3 pathways) including any members of the PDGF family such as PDGF-A, -B, -C and -D, and either homo- or heterodimers (e.g. PDGF-AA, -AB, -BB, -CC, -DD). In addition to PDGF, PDGF analogues are known and include for example 740 Y-P (PDGFR 740Y-P).The PDGF can be PDGF-AA, PDGF-AB, PDGF-BB and/or PDGF-CC. Preferably mammalian and more preferably, the PDGF when used with human cells is human PDGF. The PDGF is in an embodiment, PDGF-AA. In an embodiment, the NEM comprising PDGF-AA comprises about 20-30 ng/ml PDGF-AA. Recombinant human PDGF-AA can be obtained from various commercial sources such as ProSpec Hamada St. 8 Rehovot 7670308 Israel (e.g., Catalogue number CRFOO1A CYT-341). Additionally, PDGF-AA from other mammalian sources such as mouse, rabbit, sheep or rat as mammalian PDGF shares a high degree of conservation (e.g. mammalian PDGF-A is conserved from 87-100%, B is 85% to 100 and C is 70% to 100 can be used interchangeably. In the present disclosure, PDGF, optionally PDGF-AA, is used as differentiation factor for ventralized neural progenitor cells progressing towards an oligodendrogenic fate.

In an embodiment, the NEM comprising thyroxine comprises about 40-60 ng/ml thyroxine. In another embodiment, a thyroxine analogue is used. The thyroxine analogue is, in one embodiment, levothyroxine sodium hydrate, which can be used in the place of thyroxine. In an embodiment, the concentration of levothyroxine sodium hydrate is about 40 ng/mL. In another embodiment, the thyroxine analogue is triiodothyronine/thyroid hormone 3 (T3). In an embodiment, the concentration of triiodothyronine/thyroid hormone 3 (T3) is about 40 to about 60 ng/mL.

The term "thyroxine" or "T4" as used herein, refers to the prohormone of the thyroid hormone triiodothyronine (T3), including all mammalian forms preferably human. It is used in this method as a differentiating factor when ventralized neural progenitor cells are stimulated towards their oligodendrogenic fate. Thyroxine can be obtained from various commercial sources such as Sigma-Aldrich Canada Co. Oakville, Ontario Canada (e.g., Catalogue number T1775).

Looking at FIG. 7, a particular embodiment of the media, factors and time periods that can be used is provided.

NEM can be replaced daily with the required factors.

The term "progenitor cell" (interchangeably referred to as precursor cells) refers to cells that have a cellular phenotype that is at an earlier step along a developmental pathway or progression than is a fully differentiated cell relative to a cell which it can give rise to by differentiation. Progenitor cells can give rise to multiple distinct differentiated cell types or to a single differentiated cell type, depending on the developmental pathway and on the environment in which the cells develop and differentiate.

In the context of a cell, the term "differentiated", or "differentiating" is a relative term and a "differentiated cell" is a cell that has progressed further down the developmental pathway than the cell it is being compared with. Thus, stem cells can differentiate to lineage-restricted precursor cells (such as a neural progenitor cell), which in turn can differentiate into other types of precursor cells further down the pathway and then to an end-stage differentiated cell, which plays a characteristic role in a certain tissue type, and may or may not retain the capacity to proliferate further.

In an embodiment, the NEM the NEM of steps b. i) and ii) is supplemented with an FGFR agonist such as FGF2. As shown for example in FIG. 7, the NEM can comprise PDGFR agonist and FGFR agonist, optionally FGF2, for the duration of the incubation from ventralized NPCs to produce o-NPCs.

The term "FGF receptor (FGFR) agonist" as used herein means a molecule that can activate FGFR (e.g. molecules that bind to FGFR and induce the dimerization of the receptor and activate the signaling P13K pathway and Ras/ERK pathway), including FGF2, FGF8 and SUN11602.

The FGFR agonist optionally FGF2 is added in some embodiments along with heparin. Other components can also be included as described herein. For example, the NEM for culturing ventralized NPCs can comprise FGF2 (e.g. at about 10-20 ng/ml), B27 supplement without RA (or equivalent such as vitamin A), heparin and N1 supplement. Reference to "without vitamin A" also means without equivalents such as RA and "without RA" also means without equivalents such as vitamin A.

The term "fibroblast growth factor 2" or "FGF2" (also known as bFGF, basicFGF or FGF-beta as well as heparin binding growth factor 2 is a member of the fibroblast growth factor family. FGF2, for example human FGF-2 can be obtained from various commercial sources such as Cell Sciences®, Canton, Mass., USA, Invitrogen Corporation products, Grand Island N.Y., USA, ProSpec-Tany Techno-Gene Ltd. Rehovot, Israel, and Sigma, St Louis, Mo., USA.

FGF2, can be replaced with other FGFR agonists such as FGF2 or FGF8. Other FGFR agonists are described in US Patent Application 20150011579, titled *FGF Receptor (FGFR) Agonist Dimeric Compounds, Process for the Preparation Thereof and Therapeutic Use Thereof.*

In an embodiment, the ventralized NPCs are obtained by culturing unpatterned NPCs expressing $Sox2^+$, $Pax6^+$ and $Otx2^+$ for about 12 days (days 14 to 26 of FIG. 6) in NEM with i) retinoic acid or a retinoic acid analogue for the preliminary about 7 to 11 days and ii) a Shh agonist for the latter about 9 days (e.g. about 6 days to about 12 days). This step includes producing caudalized NPCs from the unpatterned NPCs and differentiating them to ventralized NPCs as shown for example in FIG. 6.

The Shh agonist can be used for the latter 6 to 12 days depending on cells and Shh activator used. When Shh is used, the time can be about 9 days.

The retinoic acid analogue can be for example synthetic retinoid EC23 or vitamin A.

The term "caudalized NPCs" as used herein refers to NPCs having a caudal spinal cord progenitor fate and which express Sox2, Pax6 and an increased expression of Nkx6.1 relative to un-patterned NPCs and a decreased expression of Otx2 and FoxG1 relative to un-patterned NPCs. For example, "caudalized NPCs" express Sox2, Nestin and Pax6 with equivalent level to un-patterned NPCs, and have for example at least 75% decreased level of expression for FoxG1, Otx2 and Gbx2, at least 25% increased expression Nkx6.1, and have at least 25-50% increased expression of HoxA4, HoxB4 HoxC4 and HoxC5, all relative to un-patterned-NPCs. The expression level of Nkx6.1 is for example at least 25% less than the expression level this gene compared to ventralized-NPCs.

The term "sonic hedgehog agonist" or "Shh agonist" as used herein includes recombinant sonic hedgehog, purmorphamine and SAG, which stands for Smoothened Agonist and is a chlorobenzothiophene-containing compound. Shh can also be replaced with recombinant mammalian Desert hedge hog (Dhh) or recombinant mammalian Indian hedge hog (Ihh). Activates Smoothened (SMO) can also be used.

In an embodiment, the sonic hedgehog agonist used is selected from purmorphamine, SAG and recombinant Shh polypeptide. For example when the Shh agonist is Shh the concentration used can be about 100 ng/ml. In an embodiment, the concentration of purmorphamine is about 0.5 µM to about 1 µM purmorphamine.

In an embodiment, the concentration of SAG is about 0.5 µM SAG.

In an embodiment, the concentration of Shh is about 100 ng/ml Shh.

In some embodiments, the method comprises obtaining caudalized NPCs from unpatterned NPCs expressing Sox2$^+$/Pax6$^+$ Otx2$^+$ with retinoic acid (RA) (for example at a concentration of 0.1 µM-0.2 µM) and/or a retinoic acid analogue and using caudalized NPCs to produce the ventralized NPCs.

The term "unpatterned NPCs" as used herein refers to NPCs that have yet to be caudalized and ventralized. Un-partnered NPCs are primitive or definitive NPCs which are not yet being treated with any patterning factors like RA or Shh (and its agonists). Un-patterned NPCs express Pax6, Nestin and Sox2. The level of expression of Gbx2, Emx2 and Irx2 is lower in un-patterned NPCs as compared to mid-brain identity NPCs, and the level of expression of Hox genes (like A4, B4, C4) are lower in un-patterned NPCs as compared to spinal cord identity NPCs.

Figure 5:
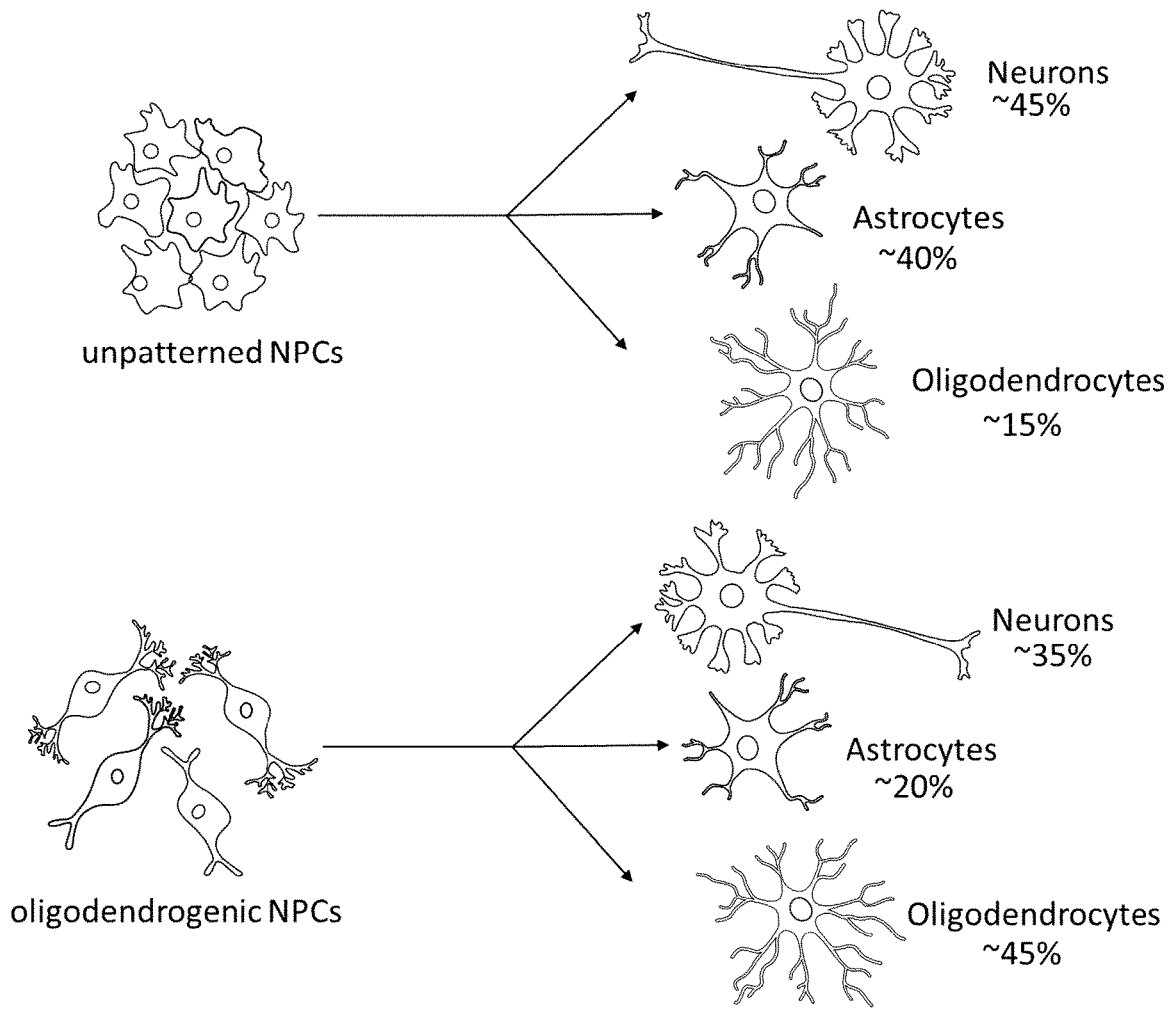
FIG. 5 NPCs are mainly differentiated to neurons and astrocytes after removal of growth factors FGF2 and EGF, however, o-NPCs are biased towards an oligodendrocytic fate and predominantly differentiate to oligodendrocytes. NPCs, neural progenitor cells; o-NPCs, oligodendrogenic neural progenitor cells.

Typically unpatterned NPCs are tripotent cells which differentiate mainly towards neuronal and astrocytic cell fates after removal of growth factors EGF and FGF2 as depicted in FIG. 5. Examination of transcription factor profiles of the NPCs indicates that the Pax6 expressing NPCs do not express Olig2 and Nkx2.2, homeodomain proteins which are expressed in ventral neural progenitors (Lu et al., 2002; Zhou, Choi, & Anderson, 2001).

As shown in the Examples, the unpatterned NPCs are cultured with RA for a period of about 3 days, followed by culturing in NEM comprising RA and a Shh agonist for about 3 days to about 9 days, for example 6 days followed by culturing in media comprising a Shh agonist without RA for about 3 days.

During treatment with RA (no FGFR agonist such as FGF2) is added to the medium although in some embodiments, EGFR agonist, optionally EGF or betacelluin is added. The culture media used for this stage can comprise B27 supplement comprising vitamin A.

The expression of specific markers can be used to determine that the unpatterned cells have been caudalized. For example, as shown in the examples quantitative RT-PCR analyses indicated that RA treatment decreased the expression of Otx2 and increased the expression of HoxA4.

For the step involving culturing with RA or retinoic acid analogue and the Shh agonist together, the unpatterned NPCs are also optionally cultured in the presence of EGF (for example at a concentration of about 10 to about 20 ng/ml) for the first 9 days. For the last 3 days, the NPCs are cultured in the presence of a Shh agonist and cultured with FGFR agonist such as FGF2. The period of caudalization and ventralization is depicted in FIG. 6 and extends from approximately day 14 to 26 of the 40 day protocol.

The removal of RA and the addition of FGFR agonist such as FGF2 for the last 3 days (e.g. days of 23 to 26 of FIG. 6) prevents for example differentiation of cells into spinal motoneurons (MNs). RA treatment of Nkx6.1+ NPC can, for example cause them to differentiate into spinal MNs. To prevent differentiation to MNs and to promote the generation of oligodendrogenic NPCs, RA is removed for example after 6 days and FGFR agonist such as FGF2 is supplemented in place of EGF. As shown herein, the removal of RA and addition of FGFR agonist such as FGF2 almost completely blocks the caudalized/ventralized cells from differentiating into MNs and promotes the generation of Olig2+/Nkx2.2+ cells.

In another embodiment, the method further includes a step of obtaining unpatterned NPCs from columnar cells in the form of rosettes and expressing Pax6

The term "rosette" as used herein refers to a cellular pattern of columnar cells. The neural rosette is the developmental signature of neuroprogenitors in cultures of differentiating embryonic stem cells; rosettes are radial arrangements of columnar cells that express many of the proteins expressed in neuroepithelial cells in the neural tube. In addition to similar morphology, neuroprogenitors within neural rosettes can differentiate into the main classes of progeny of neuroepithelial cells in vivo: neurons, oligodendrocytes, and astrocytes.

The columnar cells forming rosettes can be cultured based on Chambers et al. (2009) dual-SMAD inhibition using chemically defined adherent colony culture (e.g. neural induction media (NIM).

As used herein "neural induction media" or "NIM" herein means a base media suitable for culturing neural precursor cells such as DMEM/F12 comprising one or more of sodium pyruvate, a glutamine product such as glutamine or Gluta-MAX™, one or more antibiotics such as penicillin and/or streptomycin, a supplement such as B27 supplement without vitamin A, non-essential amino acids such as Glycine, L-Alanine, L-Asparagine, L-Aspartic acid, L-Glutamic Acid, L-Proline, L-Serine, to which BMP inhibitor such as LDN193189 or Noggin, TGFb inhibitor (such as SB431542), FGFR agonist such as FGF2, optionally heparin and EGFR agonist, optionally EGF. An example of a suitable NIM is provided in Example 1.

NEM and NIM can comprise similar components. Steps using NIM include addition of TGFb inhibitor and BMP inhibitor. Molecules which can inhibit both TGFb receptor and BMP signaling are referred to as dual SMAD inhibitors. The dual SMAD inhibitor can be any protein or small molecule that can inhibit both BMP and TGFb signaling.

As depicted in FIG. 3, induction of neural cells can be achieved by growth factors hLIF (e.g. about 10 ng/ml) accompanied by N2, B27(-RA), FGFR agonist/heparin and differentiation factors TGFb inhibitor (SB431542) (1 µM), BMP inhibitor (1 µM) (LDN193189)/or Noggin (200 ng/ml) or any one of factors mentioned in Example 1 for a period of 7 days. Following this period, rosettes are re-plated on vessels such as culture plates pre-coated with poly-L-lysine/laminin and in NEM comprising EGF (10-20 ng/ml) for 4 to 6 days as described in Example 1 and depicted in FIG. 3. At this time cells are positive for Sox2 and Otx2, a homeodomain protein expressed by fore- and mid-brain cells, but negative for HoxC4, a homeodomain protein produced by cells in the spinal cord.

Several TGFb inhibitor are known. Any compound which binds to TGFb or TGFb receptor and disrupts the interaction of ligand (TGFb) with any of the TGFb receptors (Type I, Type II and/or Type III) and prevents phosphorylation and activation of SMAD2/3 can be used. This includes TGFb inhibitors SB431542, LY2109761, LDN-193189, LY364947, SB525334 and SB505124.

For the last about 5 days of the Noggin treatment, a GSK3β inhibitor such as CHIR99021, TWS119 or LY2090314 can be used. Alternatively to using a GSK3β inhibitor, WNT, a WNT activator or WNT agonist can be used in place thereof, for example Wnt agonist 1 or SKL2001. Inclusion can increase efficiency.

In an embodiment, one or more of the culture steps is performed in a monolayer system.

The term "monolayer system" as used herein refers to a cell culturing system where cells grow in a single layer on a growth surface, for example in a plate, flask or other vessel, in the absence of feeder cells. The growth surface is a feeder-free system using for example a gelatinous matrix coated vessel such as a culture plate or dish. The gelatinous matrix can for example be gelatin, Matrigel or Geltrex.

In an embodiment, the monolayer system used to culture the ventralized NPCs comprises culturing the ventralized NPCS on gelatinous matrix coated plates.

In an embodiment, the gelatinous matrix is selected from gelatin Matrigel, or Geltrex, Vitronectin, Fibronectin or Laminin. Matrigel is a gelatinous protein mixture of secreted extracellular matrix proteins derived from mouse tumor cells and Geltrex is as a reduced growth factor basement membrane extract used for attachment and maintenance of human embryonic stem cells (hESCs) and human induced pluripotent stem cells (hiPSCs). Any mammalian extracellular or basement matrix used for NPC cell culture can be used including for example Vitronectin, Laminin or Fibronectin from any mammalian sources. Matrigel and Geltrex coated vessels can be made using Matrigel or Geltrex. Matrigel is available for example from Corning, Tewksbury Mass. 01876, USA and Geltrex is available for example from Thermo-Fisher scientific Mississauga, Ontario, Canada.

In some embodiments, the gelatinous matrix such as laminin is supplemented with a Notch signaling activator such as DLL4 or DLL1. Addition of a Notch signaling activator can improve the efficiency of generation of oNPCs.

Alternatively, a feeder-dependent culturing system can also be used, wherein cells grow on mouse embryonic fibroblast cells.

The term "poly-L-lysine/laminin" as used herein refers to a polymer of basic amino acid lysine which enhances the adherence of neural cells to the plate by changing the net charge of plates to positive. They are particularly useful for the culture of central nervous system (CNS) neurons. The L or D isomers can be used for plating, however, the D isomer may be preferred because there is no breakdown released by proteases of the cells. Laminin is an extracellular matrix constitutively used for the culture of neural cells. The plates are first coated with poly L-lysine (PLL) and then with laminin to increase the concentration of laminin applied using this method.

The term EGF receptor (EGFR) agonist as used herein means a molecule that can activate EGFR (e.g. any small molecule that binds to the EGFR and results in its dimerization EGFR tyrosine phosphorylation and activation of Ras/ERK pathway, STAT pathway and FAK pathway), including EGF, betacelluin or NSC228155.

The term "EGF" as used herein refers to mammalian Epidermal growth (EGF), for example human EGF having for example Gene Identification number (Gene ID: 1950) as well as active conjugates and fragments thereof, including naturally occurring active conjugates and fragments. Any mammalian EGF can be used including human EGF, mouse EGF, sheep EGF, rabbit EGF and rat EGF, as well as active conjugates and active fragments thereof. Human EGF is preferred.

EGF can be replaced with other EGFR agonists.

The term "active fragments" as used herein is a polypeptide having amino acid sequence which is smaller in size than, but substantially homologous to the polypeptide it is a fragment of, and where the active fragment polypeptide is about at least 50%, or 60% or 70% or at 80% or 90% or 100% or greater than 100%, for example 1.5-fold, 2-fold, 3-fold, 4-fold or greater than 4-fold as effective in terms of biological action as the polypeptide from which it is a fragment of. Examples include fragments of EGF which bind and activate EGF receptor.

In an embodiment of the present disclosure, the columnar cells forming rosettes are cultured a monolayer system.

Figure 8:
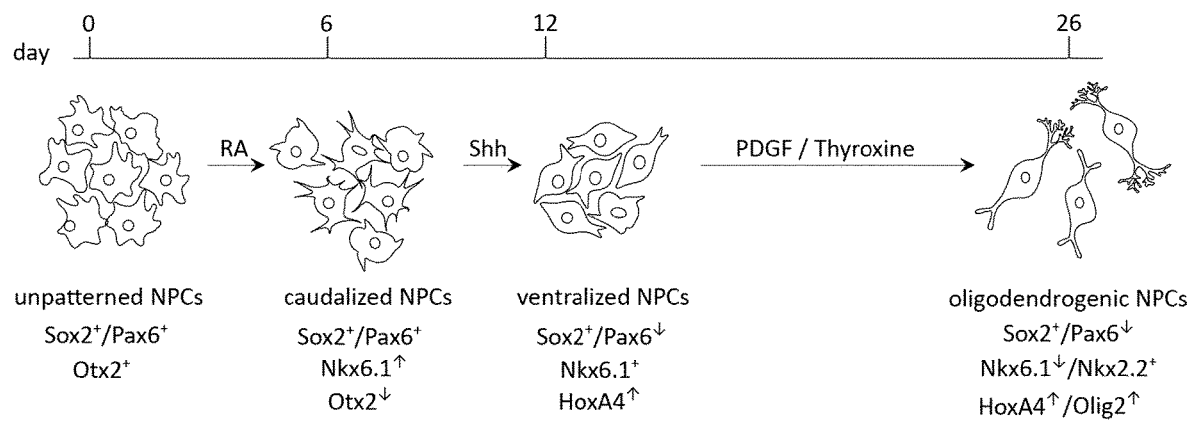
FIG. 8A Overview of the generation of o-NPCs from hiPSCs-NPCs.
FIG. 8B Changes in the gene expression profile of key transcription factors during generation of o-NPCs from un-patterned NPCs.
FIG. 8C Changes in the morphology of un-patterned NPCs to bi-polar morphology of o-NPCs cultured on laminin.
FIG. 8D o-NPCs have the potential to be differentiated to all three different cell types; neurons (β-III Tub), astrocytes (GFAP) and oligodendrocytes (CNPase).
FIG. 8E q-RT-PCR gene expression analysis of o-NPCs as it compared to hiPSCS.
FIG. 8F Differentiation profile of o-NPCs. Majority of o-NPCs differentiating towards oligodendrocytes.
Figure 8:
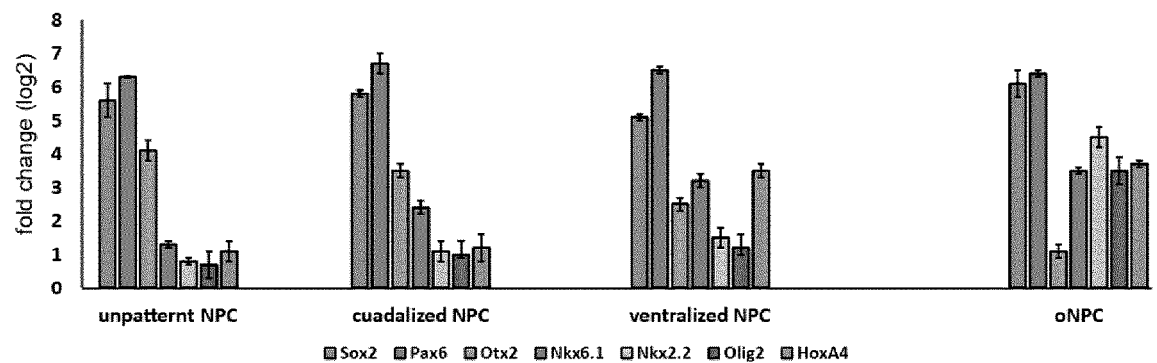
Figure 8:
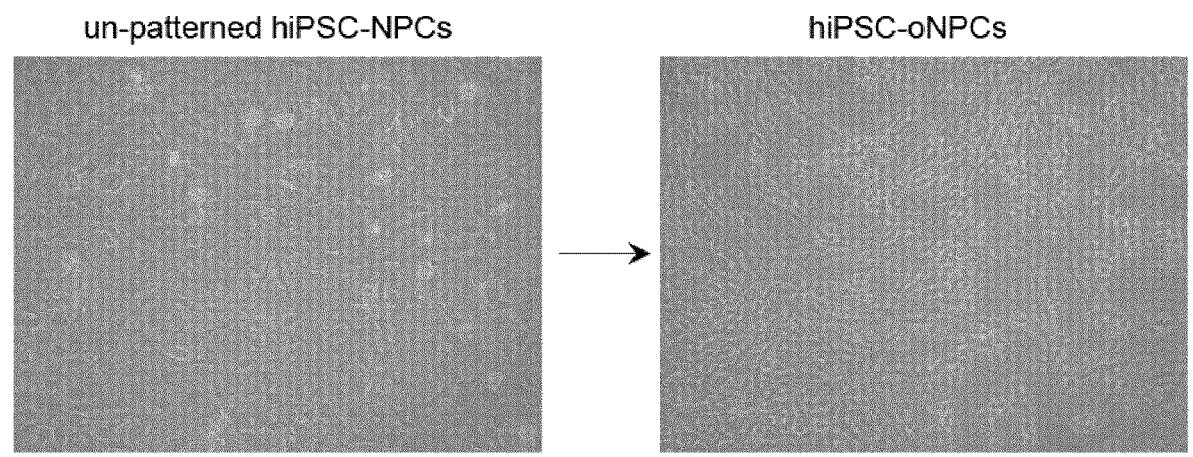
Figure 8:
Figure 8:
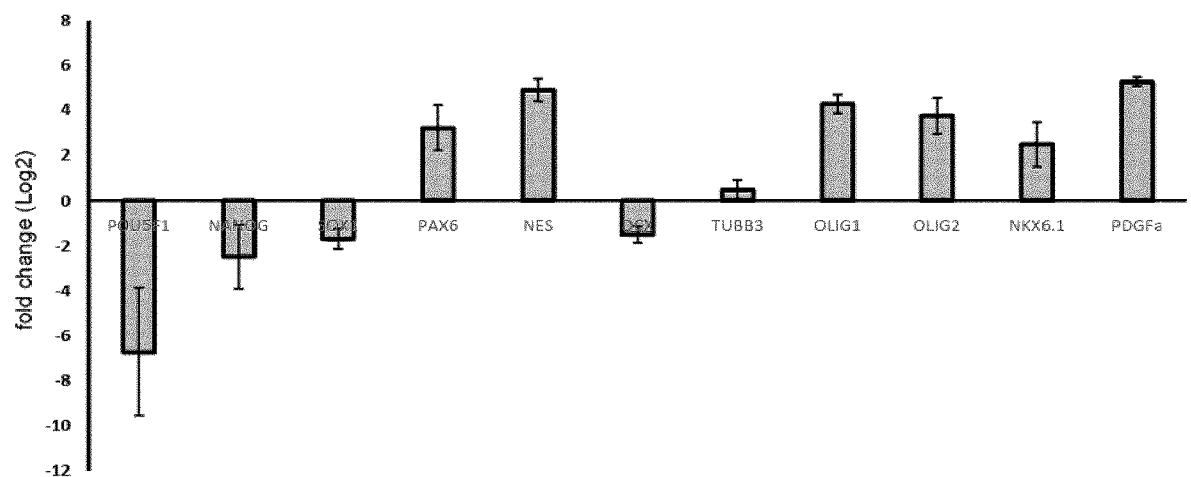
Figure 8:
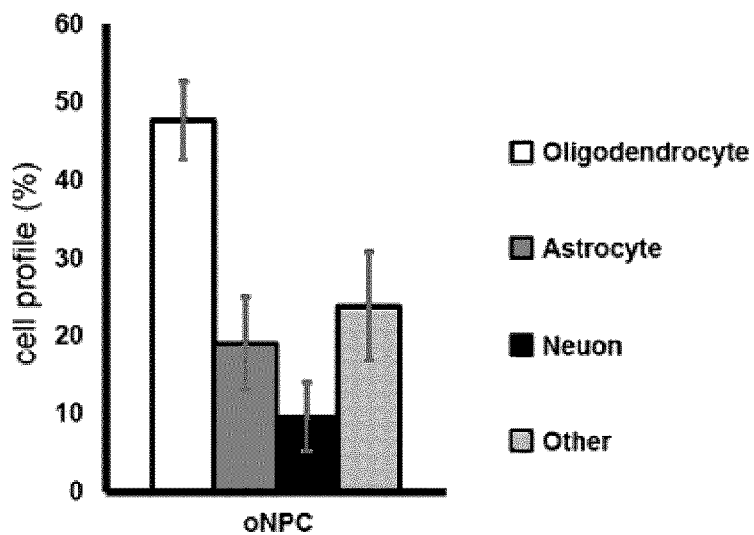

In a further embodiment, the columnar cells in the form of rosettes are obtained from human pluripotent stem cells (PSCs), optionally human induced PSC (hiPSCs) or human embryonic stem cells (hESCs). Any hiPSC or hESC line can be used in the methods described herein including for example any fetal or adult derived human NPCs including directly reprogrammed NPCs (drNPCs) (e.g. day 14 cells in FIG. 1 or day 0 cells in FIG. 8. Examples of hiPSC cell lines that can be used include 1.53 and BC1. The BC1 cell line one is derived from adult bone marrow CD34+ cells and the 1.53 line which is derived from human fibroblasts using piggyBac vectors.

The term "pluripotent stem cell" as used herein refers to a cell with the capacity, under different conditions, to differentiate to more than one differentiated cell type, and for example the capacity to differentiate to cell types characteristic of the three germ cell layers, and includes embryonic stem cells and induced pluripotent stem cells. Pluripotent cells are characterized by their ability to differentiate to more than one cell type using, for example, a nude mouse teratoma formation assay. Pluripotency is also evidenced by the expression of embryonic stem (ES) cell marker.

The term "stem cell" as used herein, refers to an undifferentiated cell which is capable of proliferation, self-renewal and giving rise to more progenitor cells having the ability to generate a large number of mother cells that can in turn give rise to differentiated or differentiable daughter cells. The daughter cells can for example be induced to proliferate and produce progeny that subsequently differentiate into one or more mature cell types, while also retaining one or more cells with parental developmental potential.

In an embodiment, the pluripotent stem cell is from a mammal, such as a human. In an embodiment, the pluripotent stem cell is a human iPSC (hiPSC).

Further, ROCK inhibitors can be used when the cells are passaged to improve cell survival. For example, a ROCK inhibitor (e.g. Y-27632) can be used for the first 24 hours after each cell passaging in the entire method of producing o-NPCs from hiPSC-NPCs for example as described in Example 1. In an embodiment, the ROCK inhibitor Y-27632 at a concentration of 10 µM is used. In other embodiments a JAK inhibitor such as Jak inhibitor I is used instead of a ROCk inhibitor. For example JAKi I can be used at a final concentration 1 µM instead of the ROCK inhibitor.

The term "passaging", "passaged" or "passage" as used herein refers to transferring the cultured cells from their current growth medium to a new growth medium. Cells can be passaged for example according to as described in Example 1. Any suitable method of passaging however can be used. For example hIPSCs should be passaged in order to avoid overgrowth and to maintain them in an undifferentiated state. Further it may be preferable to passage iPSCs in clumps.

As a person skilled in the art would understand, cells can be dislodged from the culture plate with the use of enzymes and enzyme cell detachment solutions such as the enzyme cell detachment solution Accutase™. Other enzymes like Dispase or TrypLE can also be used.

o-NPCs generated using methods described herein can be expanded for example for up to three passages without losing their proliferation and differentiation capacity. After this stage the proliferation rate of the cells may slow and they eventually cease proliferating for example at passage 5 to 6 when they morphologically appear as flat, expanded cells.

Using the methods described herein, one can produce a population of tripotent o-NPCs differentiated from hiPSC-NPCs, the population comprising for example about 90% to about 95% o-NPCs based on immunocytochemical Olig2 staining.

The o-NPCs made using the protocols described herein can produce spinal oligodendrocytes and can be used in various applications.

Looking at FIG. 1 which outlines the stages of development from iPSCs to o-NPCs, the period corresponding to differentiating ventralized NPCs to o-NPCs extends approximately from day 26 to day 40, the period corresponding to differentiating unpatterned NPCs to ventralized NPCs is from day 14 to 26, the period corresponding to differentiating columnar cells in the form of rosettes to unpatterned NPCs is from day 10 to 14 and the period of differentiating iPSCs to rossettes is from day 2 to 10.

Accordingly, in an embodiment, the method of producing o-NPCs comprises
  a) obtaining iPSCs cultured for at least about 2 days (days 0-2 in FIG. 3);
  b) culturing the iPSCs:
    i. in NIM supplemented with leukemia inhibitory factor (LIF), FGFR agonist, B27 lacking vitamin A, N2 supplement, TGFb inhibitor, BMP inhibitor, optionally Noggin, AMP-activated protein kinase (AMPK), inhibitor optionally compound C or Dorsomorphin for about 7 days (day 2 to day 9 in FIG. 3); and
    ii. in NIM supplemented with EGFR agonist, FGFR agonist, B27 supplement lacking vitamin A and N2 supplement, wherein the iPSCs are cultured in vessels coated with a gelatinous matrix comprising poly-L-lysine/laminin for about 1 to 2 days to produce columnar cells in the form of rosettes expressing Pax 6 (day 10 in FIG. 3);
  c) culturing the columnar cells in the form of rosettes from step b. in NEM comprising EGFR agonist, FGFR agonist, B27 supplement lacking vitamin A and N2 supplement for about 4 days, wherein the iPSCs are cultured in vessels coated with a gelatinous matrix comprising poly-L-lysine/laminin, to produce unpatterned NPCs (day 14 in FIGS. 3 and 6);
  d) culturing the unpatterned NPCs from step c. for about 6 days (optionally 3 to 9 days) in NEM comprising retinoic acid and/or a retinoic acid analogue such as synthetic retinoid EC23, N2 supplement, B27, EGFR agonist and a Shh agonist to produce caudalized NPCs (day 20 in FIG. 6);
  e) culturing the caudalized NPCs from step d.:
    i. in NEM comprising EGFR agonist, N2 supplement, B27 supplement, retinoic acid and/or a retinoic acid analogue and Shh agonist for about 3 days (days 20 to 23 of FIG. 6); and
    ii. in NEM comprising FGFR agonist such as FGF2, N2 supplement, B27 supplement and a Shh agonist for about 3 days (days 23 to 26 of FIG. 6) to obtain ventralized NPCs;
  f) culturing the ventralized NPCs for about 12 to about 16 days (days 26-40 of FIG. 7) in NEM comprising i) PDGFR agonist for the about 12 to about 16 days; ii) B27 and N1 supplement for the preliminary about 12 days; and iii) thyroxine for the latter about 7 to about 9 days, to produce o-NPCs.

The term "cell culture medium" (also referred to herein as a "culture medium" or "medium") as referred to herein is a medium for culturing cells containing nutrients that maintain cell viability and support proliferation and optionally differentiation. The cell culture medium may contain any of the following in an appropriate combination: salt(s), buffer(s), amino acids, glucose or other sugar(s), antibiotics, serum or serum replacement, and other components such as peptide growth factors, vitamins etc. Cell culture media ordinarily used for particular cell types are known to those skilled in the art.

The term "N2 supplement" as used herein is used to refer to a hormone mix comprising transferrin, insulin, putrescine, selenium and prodesterone. For example the N2 supplement can comprise 10 mg/ml Transferrin, 2.5 mg/ml Insulin, 1 mg/ml Putrescine, 1 ul/ml Selenium, 1 ul/ml Prodesterone.

The term "N1 supplement" as used herein insulin, transferrin, selenium, putrescein and progesterone. For example the N1 supplement can comprise 0.5 mg/ml recombinant human insulin, 0.5 mg/ml human transferrin (partially iron-saturated), 0.5 µg/ml sodium selenite, 1.6 mg/ml putrescine, and 0.73 µg/ml progesterone.

The suitable culture medium can include a suitable base culture medium including for example, NIM and NEM including the formulations described herein and/or any other or media that supports the growth of cells to provide for example a base culture medium composition to which components and optionally other agents can be added.

As mentioned, the oNPCs are biased to produce oligodendrocytes. Accordingly, also provided is a method of producing a population of cells comprising oligodendrocytes, the method comprising:

i) producing o-NPCs according to a method described herein;

ii) differentiating the cells wherein the step of differentiating optionally comprises a) culturing in NEM lacking EGFR agonist and FGFR agonist supplementation and comprising low serum, optionally about 0.1% FBS to about 1% FBS, optionally for about 7 to 15 days, optionally 10 days to promote formation of oligodendrocytes.

The o-NPCs can also be used to produce a mixed population of cells or promote formation of radial glial cells expressing for example 3CB2, by culturing the o-NPCs in NEM lacking FGFR agonist such as FGF2 and EGF agonist supplementation optionally for about 7 to 15 days.

In certain embodiments, the method further comprises enriching and/or isolating the desired cells.

Cells and Compositions and Methods of Use

Also provided is a population of cells produced according to a method described herein. In an embodiment, the population of cells is comprised in a composition optionally comprising a carrier, optionally a pharmaceutically acceptable carrier.

As used herein, the term "pharmaceutically acceptable carrier" is intended to include any and all solvents, media, isotonic and absorption delaying agents, and the like, compatible with pharmaceutical administration and for use with cells. Optional examples of such carriers or diluents include, but are not limited to, buffered saline, culture media, ringer's solutions, dextrose solution, and 5% human serum albumin and bovine serum albumin (BSA).

In an embodiment, the cell population is an enriched or isolated cell population. For example it can be enriched to exclude cells that do not share the desired combination of markers.

The term "isolated population of cells" as used herein refers to a population of cells that has been removed and separated from a mixed or heterogeneous population of cells. In some embodiments, an isolated population is a substantially pure population of cells as compared to the heterogeneous population from which the cells were isolated or enriched from, for example at least 90% pure.

In an embodiment, the population is a clonal population derived from a single cone.

The population of cells can comprise oNPCs, or cells differentiated therefrom.

The population of cells can isolated, purified and/or diluted in culture media, including the medias described herein or freezing solution (such as culture medium with glycerol and the like). The composition can be frozen. In particular, unpatterned NPCs can be frozen for long periods of time (on the order of years).

The cells can for example be dissociated as single cells, optionally a clonal single cell suspension in culture media such as NIM or NEM described herein. The cells can also be injected in any type of pharmaceutically acceptable, carrier, matrix or pharmaceutically acceptable vehicle.

Accordingly also provided is a pharmaceutically acceptable matrix, such as a gel matrix, comprising the population of cells produced as described herein. Also provided in another aspect is a kit comprising PDGFR agonist and thyroxine and/or a thyroxine analog and optionally and other component used in method herein, optionally for preparing o-NPCs.

In some embodiments, the population of cells are for use in transplantation in a recipient in need thereof. Such population of cells are resuspended using sterile and/or GMP grade pharmaceutically acceptable carriers such as sterile cell culture media.

As shown in the Examples, the population of cells produced using a method described herein can be used to treat spinal cord injuries. For example it is demonstrated that the population of cells described can be used to treat acute cervical and thoracic SCI as well as chronic thoracic SCI. The population of cells can also be used for treating chronic cervical spinal injuries, the treatment of multiple sclerosis (MS), and cerebral palsy (CP) as well as other demyelination diseases.

Also included in other aspect are uses of said cells and compositions comprising said cells for transplanting and/or treating a subject in need thereof, for example for transplanting and/or treating a subject with a SPI or a demyelination disease, optionally MS or CP.

The term "subject" as used herein includes all members of the animal kingdom including mammals, and suitably refers to humans.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments and combinations thereof for treating SPI or other neural conditions that would benefit from an infusion of oligodendrocytes. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

As used herein, the terms "administering," "introducing" and "transplanting" are used interchangeably in the context of delivering a population of o-NPCs or their differentiated progeny into a subject, by a method or route which results in at least partial localization of the introduced cells at a desired site. The cells can be implanted directly to the spinal cord, or alternatively be administered by any appropriate route which results in delivery to a desired location in the subject where at least a portion of the implanted cells or components of the cells remain viable.

For traumatic injuries the cells can be administered 2 weeks or longer after the injury.

The cells can be administered in culture media, optionally NEM or comprised in a pharmaceutically acceptable matrix, optionally a gel matrix.

Cells can be induced from the somatic cells of a subject to be treated. In an alternate approach oNPCs produced from an allogeneic donor are used to for example generate a bank of oNPCs with different HLAs. HLA matched oNPCs or cells differentiated therein are then administered to the subject in need thereof.

The above disclosure generally describes the present application. A more complete understanding can be obtained by reference to the following specific examples.

These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Passaging and Maintenance of Human Induced Pluripotent Stems Cells in Culture.

This protocol is used for the long-term maintenance of hiPSCs. Various methods of passaging and maintenance can be used. Provided herein is a method that can be used.

hiPSCs can be continuously grown on plates for over 2 years without the acquisition of an abnormal karyotype. Media is changed about daily and cells are passaged once they reach about 60-80% confluency. hiPSCs can be cultured using feeder dependent culture on mouse embryonic fibroblast (MEF) cells or feeder-free culture on Matrigel or Geltrex. For feed-dependent culture, refer to Takahashi & Yamanaka, 2006.

Commercially available pre-prepared medium, mTeSR1™ available from Stem Cell Technologies (Vancouver CA) was used. An alternative is StemPro™ (Thermofisher). Other hiPSC culture media, either feeder dependent or feeder free, can also be used. Most pre-prepared hiPSC culture media contain IGF1, heregulin1, FGF2, and activin A, to maintain pluripotency.

Materials
  Protein matrix of laminin, nidogen, collagen and/or heparan sulfate proteoglycans, such as Matrigel™
  Human induced pluripotent stem cells (hiPSCs)
  Human pluripotent stem cell media such as mTeSR1 medium
  Detachment solution, optionally Trypsin, Papain or Accutase™ enzyme detachment solution
  DMEM/F12 culture medium
  ROCK inhibitor Y-27632 (other ROCK inhibitors can be used)
  Growth medium without ROCK inhibitor 1. On the day of passaging, medium can be exchanged with freshmTeSR1 medium and cells can be incubated for about 1 hr. Human induced pluripotent stem cells are passaged in order to avoid overgrowth and to maintain them in an undifferentiated state.
2. Replace growth medium with detachment solution such as Accutase. Incubate at about 37° C., for about 5 min. If cells are examined using a microscope at this stage, the edges of individual colonies should begin to lift off the plate while the center remains attached.
3. Replace Accutase with DMEM/F12. Alternate methods of passaging other than the enzymatic method described here can also be used. Other enzymes like Dispase or TrypLE can also be used.
4. Using a cell scraper (rubber policeman), gently and mechanically dissociate colonies into small pieces and transfer them to for example a 15-ml Falcon tube.
5. Centrifuge for example at 500×g, 2 min at room temperature. Aspirate supernatant and re-suspend colonies in growth medium (G mTeSR1). Titrate colonies to break them up into smaller clumps by pipetting up and down a few times.
6. Replete clumps for example in a 1:6 clumps/plate surface area ratio onto Matrigel-coated plates (see example 3). Add ROCK inhibitor (10 µM) to the medium. On the following day, change medium to growth medium without ROCK inhibitor. ROCK inhibitors (10 µM) can be used after each passage for the first 24 hr. JAK inhibitor I (JAKi; final concentration 1 µM) can also be used instead of ROCK inhibitor.
7. mTeSR1 medium can be replaced daily until the colonies have grown and started to touch each other. Some moderate differentiation may appear during this phase at the contact border between colonies. Any differentiated cells can be removed by scraping off with a sterile needle under a microscope prior to changing the medium. The hiPSCs cells should be split in a ratio of about 1:3 to 1:6 every 3 days or so. The hiPSCs cultured using this method exhibit a uniform undifferentiated phenotype.

Differentiation of Human Induced Pluripotent Cells to Neural Precursor Cells

The protocol presented here is based on Chambers et al. (2009) dual-SMAD inhibition using chemically defined adherent colony culture. The first day medium in this protocol uses ROCK inhibitor (e.g. Y27632). Induction is achieved by LIF, Noggin (or other BMP inhibitor), GSK3 β inhibitor (e.g. CHIR99021) and TGFβ-receptor inhibitor (e.g. SB431542) which drive hiPSCs towards a neuroglial lineage.

Materials
  Human induced pluripotent stem cells (hiPSCs)
  Leukemia inhibitory factor (LIF)
  Detachment solution such as Accutase or Trypsin
  Culture media such as DMEM/F12 media
  Non-essential amino acids
  B-27 supplement (or equivalent) without vitamin A
  N2 supplement
  Y27632 (or other ROCK inhibitor)
  Noggin (or other BMP inhibitor)
  CHIR 99021 (GSK3 β inhibitor)
  Compound C or Dorsomorphin (AMP Kinase inhibitor)
  SB431542 (or other TGFβ-receptor inhibitor)
  Neural induction medium
  Neural expansion medium
  Trypan Blue
  Protein matrix coated plates, optionally Matrigel-coated plates (example 3)
  Coverslips (optional)

1. Prepare Matrigel coated plates (example 3) or other protein coated plates and pre-warm neural induction medium (NIM) and dissociation solution optionally Accutase to 37° C.
   NIM used is prepared with DMEM/F-12, sodium pyruvate, GlutaMAX, penicillin/streptomycin, B27 supplement without vitamin A, non-essential amino acids (NEAA), Noggin (200 ng/ml), and FGF2 (20 ng/ml), EGF (20 ng/ml).
2. Estimate volume of NIM required for initial seeding and supplement with 10 µM Y-27632 (ROCK inhibitor).
3. Inspect hiPSCs and mechanically remove any areas of differentiated cells. Starting with a homogenous and healthy hiPSC culture will achieve a higher yield with purer NPCs.
4. Add 3 ml Accutase and incubate at 37° C., 5 min.
5. After the incubation period, remove Accutase and add fresh DMEM/F12. Gently dissociate cells that are still attached by pipetting medium, then triturate by pipetting up and down to make single cells.
6. Add 5 ml plain DMEM/F12 and collect cells in a 50-ml Falcon tube.
7. Count viable cells using Trypan Blue and a hemocytometer or automated counting platform.
8. Re-suspend cells in an appropriate volume of NIM supplemented with 10 µM ROCK inhibitor to achieve a seeding density of about 250,000 cells/cm². (for example between about 200,000 cells/cm² and 300,000 cells/cm²). Seed cells onto Matrigel-coated plates or coverslips.

9. Replace medium daily with fresh NIM supplemented with morphogens and growth factors as indicated in FIG. 3. ROCK inhibitor is not required after seeding. The first sign of differentiation to neural lineage is the appearance of columnar cells forming rosettes in the center of the colonies 8 to 10 days after culturing in NIM. The columnar cells in the rosettes, but not the flat cells in the outgrowth area, are positive for Pax6. After this step, remove all dual SMAD inhibitors (e.g. all TGFb and BMP inhibition) (FIG. 3). Dual SMAD inhibitors refer to inhibitors of BMP and TGF-beta. For BMP inhibitor Noggin (100 ng/ml to 500 ng/ml) or LDN193189 (0.1 to 1 µM) can be used. For TGF-beta inhibitor SB431542 (1-501 µM), can be used.

Figure 4:
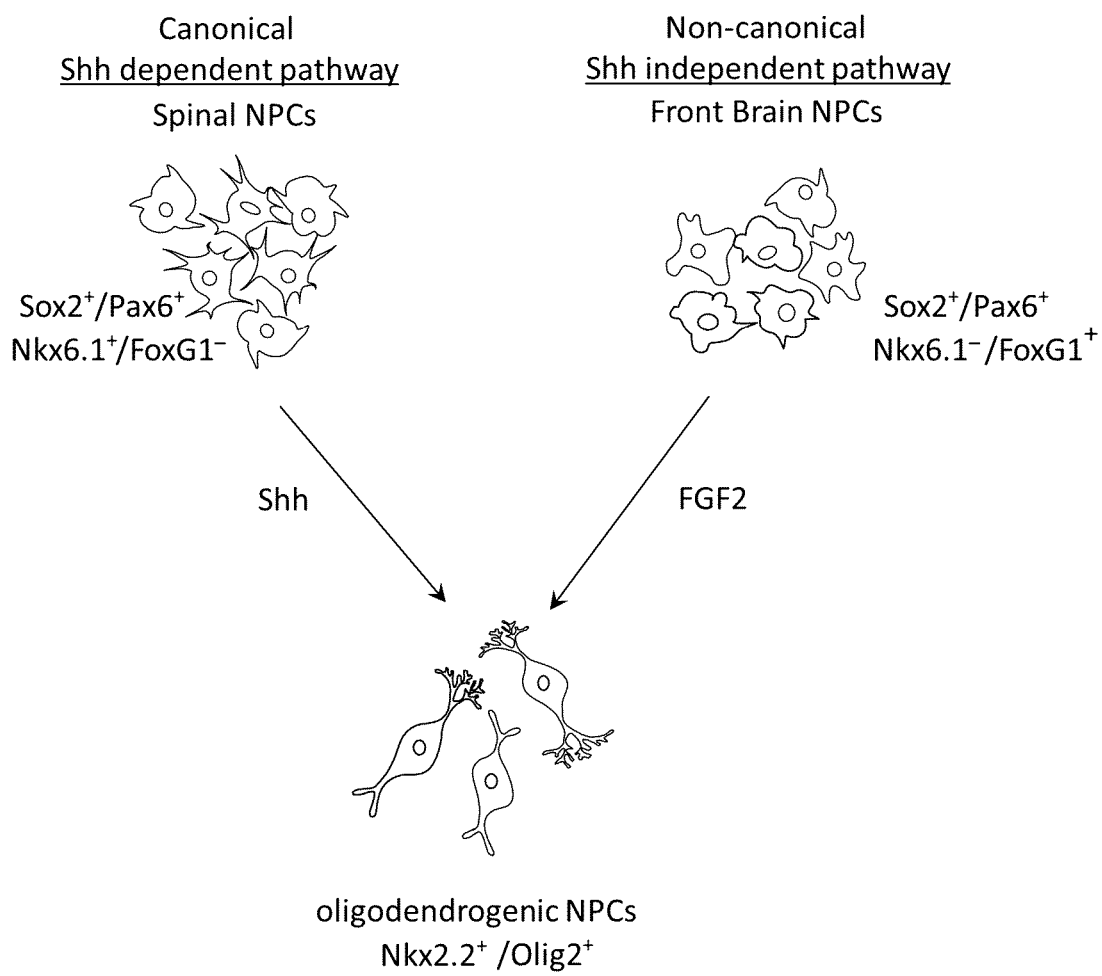
FIG. 4 Two key pathways have been proposed for generation of oligodendrogenic NPCs: (1) the canonical pathway which is dependent on sonic hedgehog (Shh) and is mainly used for generation of spinal oligodendrocytes and (2) the non-canonical pathway which is Shh independent and requires FGF2 to generate forebrain oligodendrocytes.

10. Detach neural tube-like rosettes at day 15 of differentiation mechanically and culture in suspension in the same medium. It is also possible to isolate neural rosettes by using mild Accutase (1:1 with DMEM/F12) for 15 min. This method removes the neural rosettes without the outer non-neural cells. After 15 min neural rosettes will be detached and surrounding cells will remain attached. Purity can be increased by manually selecting rosettes and plating at about 250,000 cells/cm². (for example between about 200, 000 cells/cm² and 300,000 cells/cm²) 11. Re-plate rosettes on culture dishes pre-coated with poly-L-lysine/laminin (see example 3). After 4 to 6 days in NIM, cells will be positive for Sox2 and Otx2, a homeodomain protein expressed by fore- and mid-brain cells, but negative for HoxC4 (FIG. 4), a homeodomain protein produced by cells in the spinal cord. At this point, cultures will be confluent and ready for passage for example using Accutase or TrypLE.

12. Maintain NPCs in NIM until passage about 3 (e.g. for about 10-12 days) and in NEM thereafter. By default the hiPSC-NPCs generated with this method have a dorsal anterior identity. NEM is prepared for example with DMEM/F12, sodium pyruvate, GlutaMAX, penicillin/streptomycin, B27 supplement without vitamin A, 40 ng/ml FGF2, 40 ng/ml EGF and 2 ug/ml heparin.

Differentiation of Human Induced Pluripotent Stem Cell-Derived Neural Precursor Cells to an Oligodendrogenic Fate NPCs that have been generated according to the above protocol are tripotent cells which differentiate mainly towards neuronal and astrocytic cell fates after removal of growth factors EGF and FGF2 (FIG. 5). Examination of transcription factor profiles of the NPCs at this stage indicates that the Pax6 expressing NPCs do not express Olig2 and Nkx2.2, homeodomain proteins which are expressed in ventral neural progenitors (Lu et al., 2002; Zhou, Choi, & Anderson, 2001). This intrinsic or default rostral identity indicates a need for patterning by caudalization and ventralization to generate spinal oligodendrogenic NPCs. In the following procedure, a method for patterning hiPSC derived NPCs towards a more oligodendrogenic cell fate using key morphogens is described.

Materials
Accutase or TrypLE
Retinoic acid (RA) (or any RA analogue such as synthetic retinoid EC23)
B-27 supplement with vitamin A (RA or RA analogue)
B-27 supplement without vitamin A
Sonic hedgehog (Shh) or other Shh agonist
N2 supplement
N1 supplement
PDGFR agonist such as PDGF-AA
FGFR agonist such as
EGF agonist such as EGF
Heparin
Thyroxine or triiodothyronine/thyroid hormone 3 (T3)
Matrigel-Coated Plates 1. Dissociate NPCs with Accutase or TrypLE and culture single cells at a density of about 100,000 cells/cm² on Matrigel-coated plates (see example 3). Use culture medium supplemented with caudalizing factor retinoic acid (RA; 10 µM) and/or a retinoic acid analogue such as synthetic retinoid EC23 for about 9 days. During treatment with RA, no FGFR agonist such as FGF2 should be added to the medium (EGFR agonist may be added). At this stage, B27 supplemented with vitamin A (or equivalent such as RA) can be used. Quantitative RT-PCR analyses indicate that RA treatment decreased the expression of Otx2 and increased the expression of HoxA4.

2. To pattern cells to ventral spinal progenitors, supplement medium with ventralizing morphogen sonic hedgehog (Shh; 100 ng/ml) for about 9 days. This step results in the generation of Nkx6.1+ cells. The Shh can be used from 6-12 days based on cell line and the Shh activator used. About 6 days of Shh treatment overlap with RA supplementation (FIG. 1). The resulting Nkx6.1+ cells can, by default, be differentiated into spinal motoneurons (MNs). To prevent differentiation to MNs and to promote the generation of oligodendrogenic NPCs, RA should be removed after 6 days which overlaps with Shh (or 9 days in total) and FGF2 should be supplemented in place of EGF. The removal of RA and addition of FGF2 almost completely blocks the caudalized/ventralized cells from differentiating into MNs and they will generate Olig2+/Nkx2.2+ cells in the steps that follow. It is also possible to activate Shh signaling through the small molecules smoothened agonist (SAG; 0.5 µM) or purmorphamine (1 µM) instead of the human recombinant Shh protein.

3. Supplement culture medium with PDGF-AA (20 ng/ml) and FGF (20 ng/ml) for 14 days.

4. Seven days after the start of supplementation with PDGF-AA, add 40 ng/ml thyroxine for an additional 7 to 9 days (see FIG. 1 and FIG. 7). Oligodendrogenic cells could also be stimulated by triiodothyronine/thyroid hormone 3 (T3) as part of the intrinsic cell division timer (Barres, Lazar, & Raff, 1994). At the end stage, oligodendrogenic-NPCs are bipolar or multipolar and are Olig2+ and Nkx2.2+. All growth factors and morphogens, such as RA, Shh (or SAG), PDGF-AA, throxine, etc are preferably supplemented fresh every day.

Example 2

Figure 2:
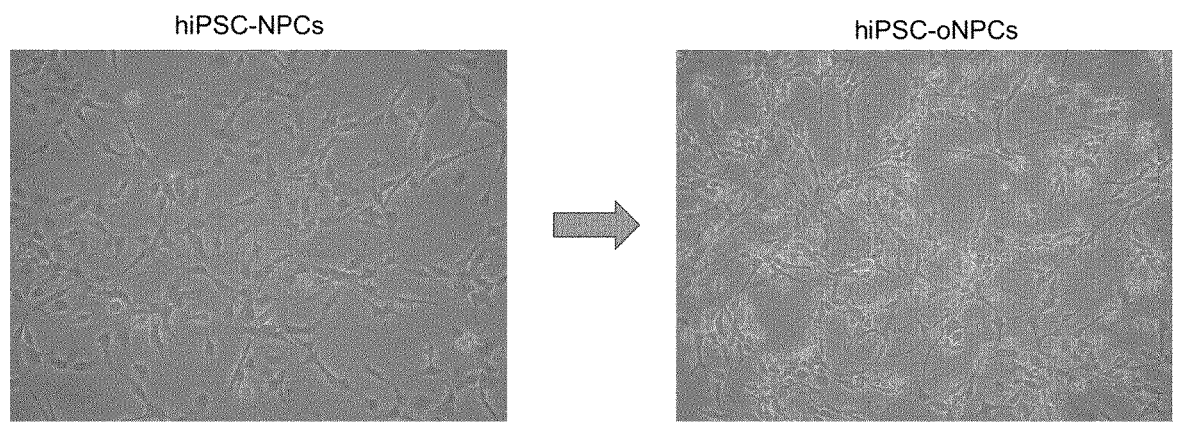
FIG. 2 Morphology of hiPSC-NPCs and hiPSC-o-NPCs. hiPSC-NPCs, human induced pluripotent stem cell-derived neural precursor cells; hiPSC-o-NPCs, human induced pluripotent stem cell-oligodendrogenic neural progenitor cells.

An overview of the method of Example 1 is provided in FIG. 1. Specifically, o-NPCs are generated from hiPSCs to produce neural tube patterning in vitro (FIG. 1; Wang et al., 2013). Retinoic acid (RA), a potent caudalizing factor, and sonic hedgehog (Shh), a ventralizing morphogen, are used at key stages to drive hiPSC-NPCs to a ventral spinal progenitor fate from days 14 to 26 in vitro. On day 23, removal of RA and addition of FGF2 are used which inhibits motor neuron differentiation. At this time, cells demonstrate elongated, mono- and bi-polar morphology (FIG. 2). These o-NPCs can be expanded for up to three passages without losing their proliferation and differentiation capacity. After this stage the proliferation rate of the cells slows and they eventually cease proliferating at passage 5 to 6 when they morphologically appear as flat, expanded cells.

Results

This protocol results in almost homogeneous cultures of o-NPCs. Cultures comprising 90% to 95% o-NPCs based on immunocytochemical Olig2 staining were obtained using this protocol. The methods presented here can typically generate up to $1\times10^7$ o-NPCs from $1\times10^5$ hiPSCs. This can be increased by expansion at the unpatterned NPC stage.

Example 3

Preparing Coated Plates

This protocol describes the preparation of Matrigel coated plates for culture of hiPSCs, NPCs, and o-NPCs. Any coated plates suitable for hiPSCs including plates coated with different matrix proteins such as laminin, collagen, heparin sulfate proteoglycans, entactin/nidogen, can be used.

Materials
  Matrigel coating (or other matrix)
  Culture medium
  Neurobasal medium (e.g. Thermoscientific Catalog number: 21103049)
  Poly L-lysine (PLL)
  Laminin
  0.15 M borate buffer (pH 8.3)
  PBS
1. Thaw one 5-ml vial Matrigel at 4° C. overnight to prevent polymerization. Matrigel matrix starts to form a gel above 10° C., therefore do not let Matrigel sit at room temperature. Geltrex can also be used instead of Matrigel.
2. The next day, dilute Matrigel in cold culture medium to a final concentration of 3 mg/ml and mix well.
3. Add 50 µl diluted Matrigel to each $cm^2$ growth area to cover the whole surface of the culture plate.
4. Warm plates with Matrigel in a 37° C. incubator 1 hr to allow Matrigel to adhere. Aspirate leftover coating solution and wash once with neurobasal medium. Plates can be used immediately or stored at 4° C. (for up to 1 week).

Poly L-Lysine and Laminin Coating

Poly L-lysine is the polymer of basic amino acid lysine which enhances the adherence of neural cells to the plate by changing the net charge of plates to positive. They are particularly useful for the culture of central nervous system (CNS) neurons. The L or D isomers can be used for plating, however, the D isomer may be preferred because there is no breakdown released by proteases of the cells. Laminin is an extracellular matrix constitutively used for the culture of neural cells. The plates are first coated with poly L-lysine (PLL) and then with laminin to increase the concentration of laminin applied using this method.

Coating with PLL
5. Prepare poly L-lysine (MW 30,000 to 70,000) at a concentration of 0.1 to 1 mg/ml in 0.15 M borate buffer (pH 8.3) and filter sterilize them using 0.2-µm filters.
6. Add enough solution to pool over the surface of the plates.
7. Incubate 2 hr at room temperature.
8. Aspirate solution and wash plates one time with PBS and proceed to coating with laminin.

Coating with Laminin
9. Prepare a stock solution of laminin by dissolving 1 mg/ml laminin in PBS. Filter sterilize using 0.2-µm filters and aliquot. Freeze aliquots at −80° C.
10. Dilute stock solution to 10 to 100 µg/ml in PBS.
11. Add enough solution to pool over the surface of the PLL-coated plates.
12. Incubate 1 hr at 37° C.
13. Aspirate to remove laminin and rinse one time with PBS.
14. Do not allow coating to dry.

Example 4

Freezing/Thawing Human Induced Pluripotent Stem Cell-Derived Neural Precursor Cells and Oligodendrogenic Neural Progenitor Cells It is preferable to cryopreserve cells when they are at their maximal growth rate.

Materials
  Human induced pluripotent stem cell (hiPSC)-derived neural progenitor cells (NPCs) and/or oligodendrogenic neural progenitor cells (o-NPCs; see example 1).
  DMSO
  DMEM/F-12 plus Glutamax
  FBS
  TrypLE Express enzyme (1×; Thermo Fisher Scientific, cat. no. 12604021)
  Neural expansion medium (NEM; see exemplary recipe in example 14)

Freezing
1. Aspirate medium from the plate.
2. Add enough dissociation solution for example Trypsin, Papain to thinly coat the entire plate.
3. Incubate at room temperature. Every 1 min, one can tap edges of plate to aid dissociation until cells have lifted off the plate. A. 4. Inhibit the ongoing enzymatic digestion.
5. Dissociate cells and collect solution in a sterile centrifuge tube.
6. Centrifuge for example at 1200×g, 4 min.
7. Aspirate supernatant.
8. Re-suspend cell pellet in culture media such as 10% FBS in DMEM/F-12 plus Glutamax and an cryopreserved rent such as 10% DMSO and transfer to cryogenic storage vials. Freeze vials.
9. Vials can be transferred to liquid nitrogen storage after 24 to 72 hr.

Thawing
10. Vial can be kept on dry ice for up to 30 min until use. Vial can be thawed in a 37° C. water bath for example until half of the contents melt to liquid.
11. Well can be filled with warmed media such as 10% FBS in DMEM/F-12 and transferred to a sterile centrifuge tube.
12. Centrifuge for example at 1200×g, 4 min
13. Aspirate supernatant and re-suspend cell pellet in NEM.
14. Plate cells onto coated plates for example Matrigel-coated plates.

Example 5

Distinct Mechanisms of Cortical- vs. Spinal Oligogenic-Neural Progenitors Derived from Human Induced Pluripotent Stem Cells for the Treatment of Cervical Spinal Cord Injury HiPSC-OPC cells produced according to the method of example 1 were characterized in vitro and in vivo in a clinically relevant clip contusion model of traumatic SCI where o-NPCs showed a strong preference for differentiation to oligodendrocytes.

Method for the Generation and Characterization of Oligodendrogenic Neural Progenitor Cell To generate oligodendrogenic NPCs (o-NPCs), from hiPSCs the Dual SMAD inhibition in monolayer culture was applied (Chambers 2009). At the start of differentiation (day 0), hiPSCs are dissociated to single cells and re-plated as a monolayer with a concentration of about 20,000 cells/cm$^2$ in mTeSR1 media, supplemented with FGF2. After cells reach 90% confluency, media is changed to induction media supplemented with Noggin (200 ng/mL) and SB431542 (10 μM) for about 7 days. For the last about 5 days, 3 μM GSK3β inhibitor (CHIR99021) is used. The resulting cells are cultured for an additional 7 days (two passages) in defined media (e.g. suitable media comprising B27 supplement or equivalent, FGFR agonist such as FGF2 and EGF agonist such as EGF on Laminin [8 μg/ml] supplemented with DLL4 (500 ng/mL) (Peprotech) to generate definitive NPCs. Defined media was DMEM/F12 with Glutamax (Life Technologies #10565-018), supplemented with 50% N2 supplement (Life Technologies #175020-01), B27 minus retinoic acid (Life Technologies #12587-010) and FGF (20 ng/ml), EGF (20 ng/ml), and heparin. The definitive NPCs are caudalized by culturing them on growth factor reduced matrigel in DMEM/F12, supplemented with 10 μM retinoic acid (RA), B27 supplement (Life Technologies, Cat #17504044), N2 supplement, and EGF (20 ng/ml) for 3 days. Cells undergo ventralization by treatment with 1 μM Shh agonist Purmorphamine (Millipore, Cat #540220) for 5 days. EGF is replaced by FGF-2 (10 ng/ml) from the media for 3 days followed by the addition of 20 ng/ml PDGF-AA (Peptrotech 100-13A) for 14 days. The resulting cells are maintained on Laminin coated dishes in DMEM/F12, B27-A, N1 supplement (Sigma Cat #N6530), PDGF-AA (20 ng/ml) and FGF-2 (20 ng/ml) for 3 more passages prior to transplantation. During passaging, 10 μM Rock inhibitor (Y-27632) is added on day 1.

Results

Figure 9:
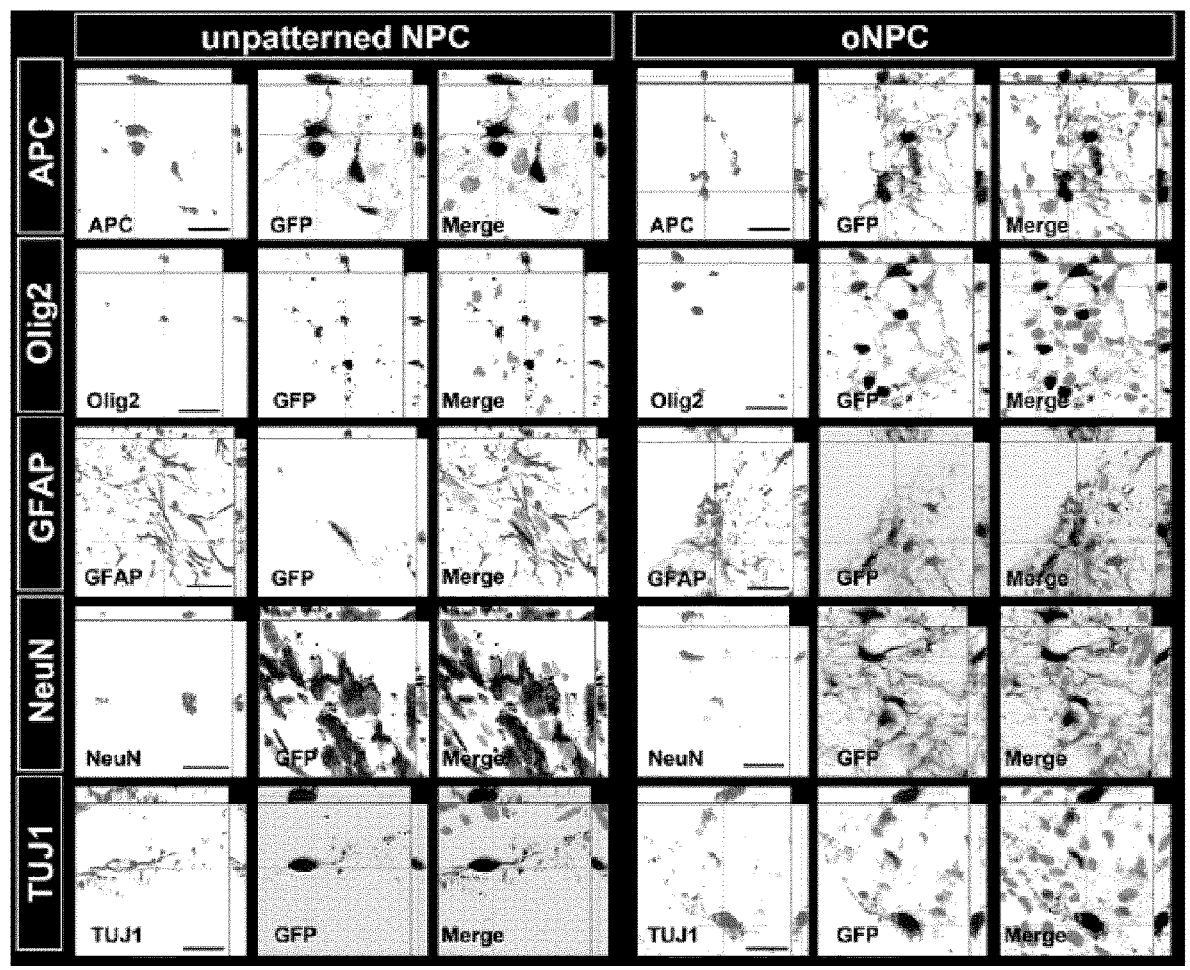
FIG. 9A Transplanted cells differentiate to express markers of mature oligodendrocytes (APC), immature oligodendrocytes (Olig2), astrocytes (GFAP) and neurons (TUJ1 and NeuN) in o-NPCs and unpatterned NPCs.
FIG. 9B Quantitative analysis of tri-lineage in vivo differentiation profiles (n=5 per each group). *p<0.05 and **p<0.01. Scale bars: 20 μm.
Figure 9:
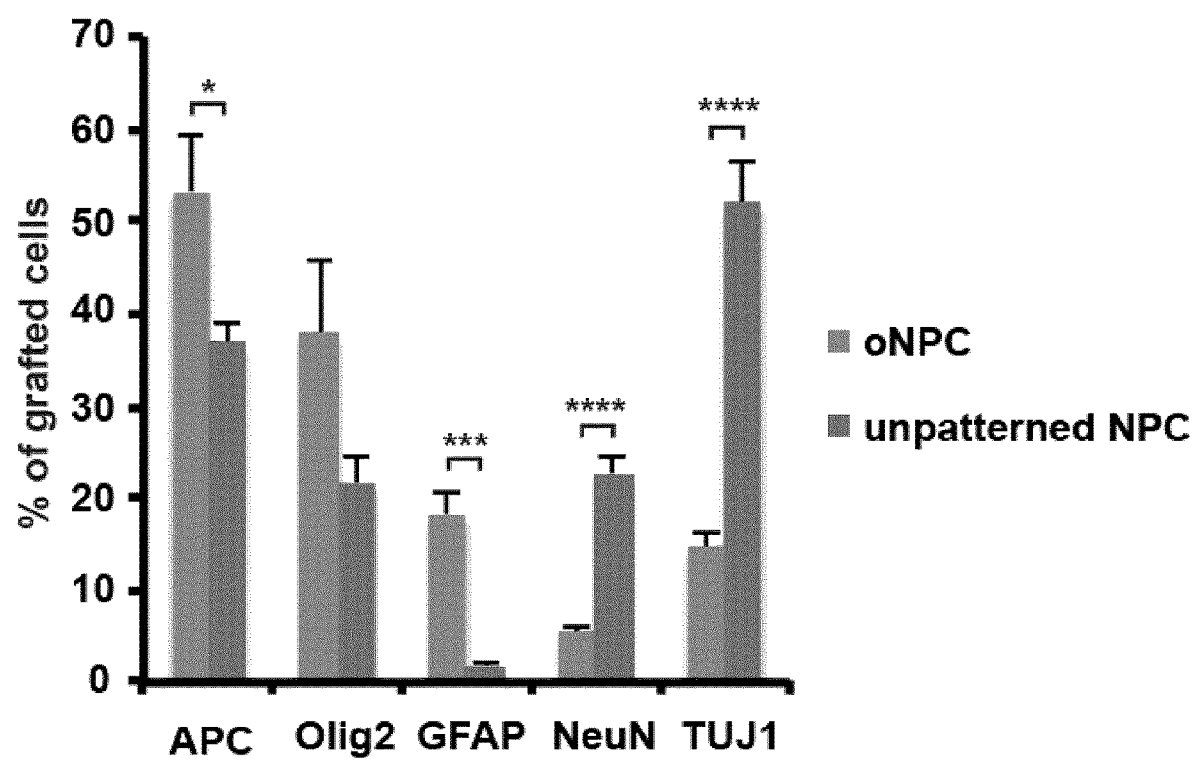

FIG. 8A shows an overview of the generation of o-NPCs from unpatterned hiPSCs-NPCs (line 1.53). Changes in the gene expression profile of key transcription factors during generation of o-NPCs from un-patterned NPCs are depicted in B. As seen in panels C and D, the morphology of un-patterned NPCs changes to bi-polar morphology of o-NPCs cultured on laminin, and further, o-NPCs have the potential to be differentiated to all three different cell types; neurons (β-III Tub), astrocytes (GFAP) and oligodendrocytes (CNPase). Finally, depicted graphically in panels E and F are the q-RT-PCR gene expression analysis of o-NPCs compared to hiPSCS, and the differentiate profile of o-NPCs. Majority of o-NPCs differentiate towards oligodendrocytes. FIG. 9A shows how transplanted cells differentiate to express markers of mature oligodendrocytes (APC), immature oligodendrocytes (Olig2), astrocytes (GFAP) and neurons (TUJ1 and NeuN) in o-NPCs and unpatterned NPCs. Finally, FIG. 9B demonstrates quantitative analysis of tri-lineage in vivo differentiation profiles (n=5 per each group). *$p<0.05$ and **$p<0.01$. Scale bars: 20 μm.

Example 6

Optimization of Morphogen Exposure

The optimal duration of caudalization and ventralization may vary depending on the parent cell line used, culture conditions, and quality of reagents. For cells with ESC origin both caudalization and ventralization are typically 1 day faster, for hiPSC derived from adult cells, the time can depend on the origin of the somatic cells. Several different types of cells have been used to produce iPSCs, including fibroblasts, neural progenitor cells, keratinocytes, melanocytes, CD34+ cells, hepatocytes, cord blood cells and adipose stem cells. In hiPSC derived from CD34+ cells caudalization and ventralization may be slower for up to 2 days. hiPSC derived from fibroblasts typically follow the time line as explained in the FIG. 1.

Example 7

Differentiation of Cells at Different Stages

Cell types can be differentiated at different stages (e.g., Nkx2.2+ and/or Olig2+ progenitors) as assessed with qRT-PCR analysis and/or immunocytochemistry.

Example 8

Figure 10:
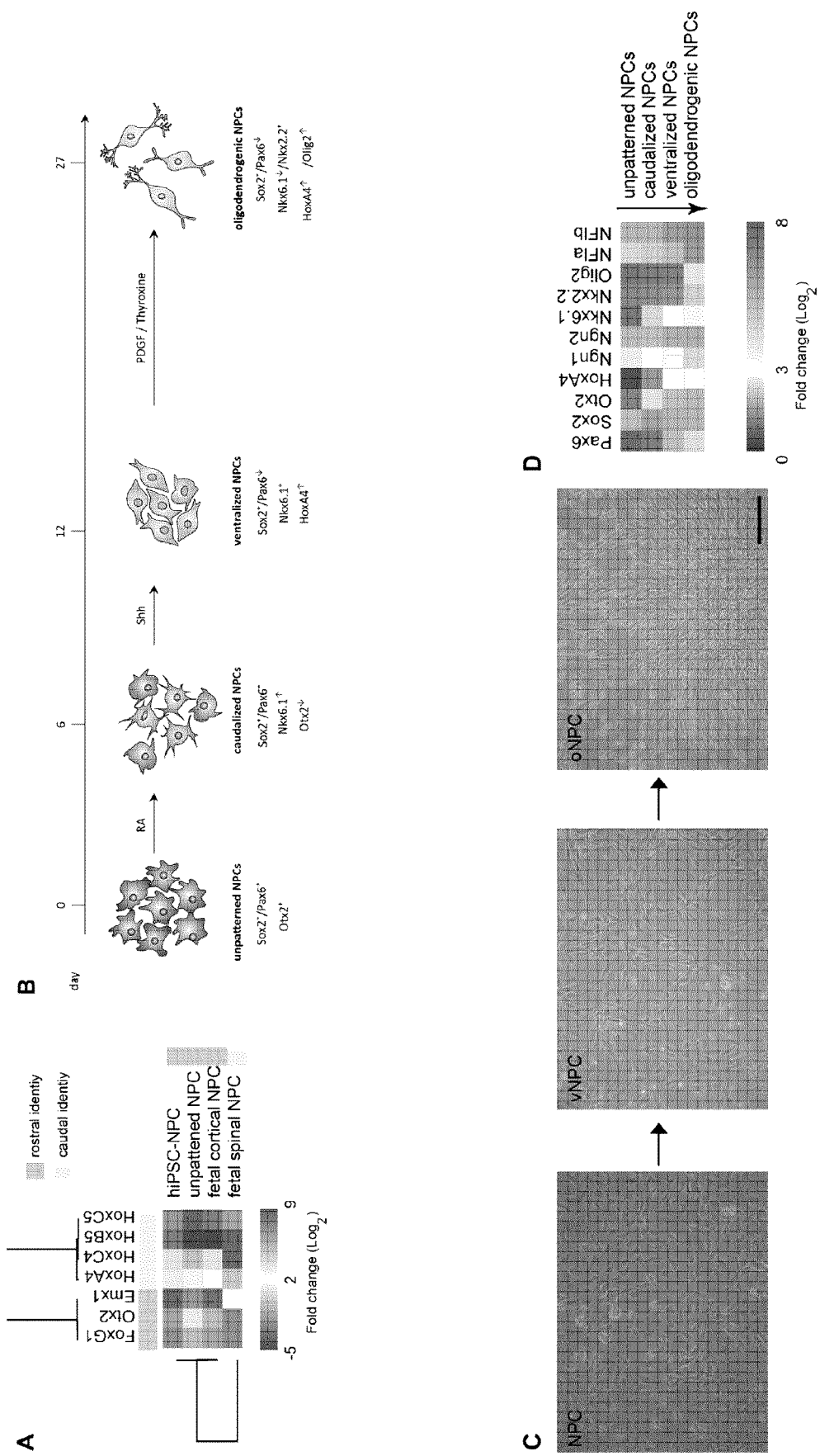
FIG. 10A-D Generation of oligodendrogenic NPCs. (A) The gene expression pattern of rostral and caudal identity markers compared between human iPSC-NPCs, unpatterned NPCs, fetal cortical NPCs and fetal spinal NPCs. Hierarchical clustering trees reveal a strong similarity between human iPSC-NPCs, unpatterned NPCs and fetal cortical NPCs while fetal spinal NPCs demonstrated caudal identity. (B) Unpatterned NPCs were caudalized using retinoic acid (RA) and then ventralized by treatment with Shh. To generate oNPCs, these cells were eventually treated with PDGF/Thyroxine. (C) Gradual changes in the morphology of NPCs after patterning towards oNPCs with elongated mono- and bi-polar morphology. These representative micrographs are from unpatterned NPC derived cells. (D) Stepwise changes in the expression profile of NPCs during generation of oNPCs. The expression of transcription factor Otx2, an important marker of brain identity, is reduced in caudalized NPCs and they gain the expression of HoxA4, a marker of spinal identity in ventralized NPCs (vNPCs). The expression of bHLH transcription factors Nkx2.2, Olig2 and Nkx6.1, is upregulated in oNPC stage.

The generation of functional neuroglial subtypes in the vertebrate CNS is a complex process with numerous key steps including the induction of neuroectoderm from embryonic ectoderm, patterning of the neural plate with regional niches along rostrocaudal and dorsoventral axes, and the differentiation of regionalized progenitor cells into post-mitotic neurons and glia. In order to generate oNPCs from human NPCs, exogenous morphogenic cues were used. To find a consensus patterning protocol, an array of factors across concentrations and time points on four different human NPC lines was tested: fetal cortical NPCs, fetal spinal NPCs, iPSC-derived NPCs and unpatterned NPCs. Both hiPSC-NPC and unpatterned NPC lines demonstrated a rostral CNS identity, similar to fetal human cortical NPCs, based on their expression levels of Otx2 and FoxG1 (FIG. 10A). Conversely, fetal spinal NPCs demonstrated expression of caudal identity markers (HoxA4, B5, C4 and C5) (FIG. 10A). To caudalize the typically rostral hNPC lines, they were treated with retinoic acid (RA), a potent caudalizing factor, for 9 days. From days 6-12, sonic hedgehog (Shh) or its agonists were used as ventralizing morphogens to drive hNPCs towards a ventral spinal progenitor fate (FIG. 10B). Fetal human spinal NPCs were only treated with Shh for 6 Days. After this time, cells acquired a spinal identity by losing expression of transcription factor Otx2, an important marker of brain identity, and gaining the expression of HoxA4, a marker of spinal identity (FIG. 10D). Cells were treated with PDGF-AA for an additional two weeks after which they demonstrated elongated monopolar and bipolar morphologies (FIG. 10C). The resulting cells expressed high levels of basic helix loop helix (bHLH) transcription factors Nkx2.2 and Olig2 (FIG. 10D). The expression of Nkx2.2 and oligodendrogenic transcription factors, such as Olig2 and Nkx6.1, were significantly upregulated in cells at this stage of oNPCs as compared to unpatterned NPCs (FIG. 10D).

Example 9 oNPCs Generate More Oligodendrocytes In Vitro than Conventional NPCs

Figure 11:
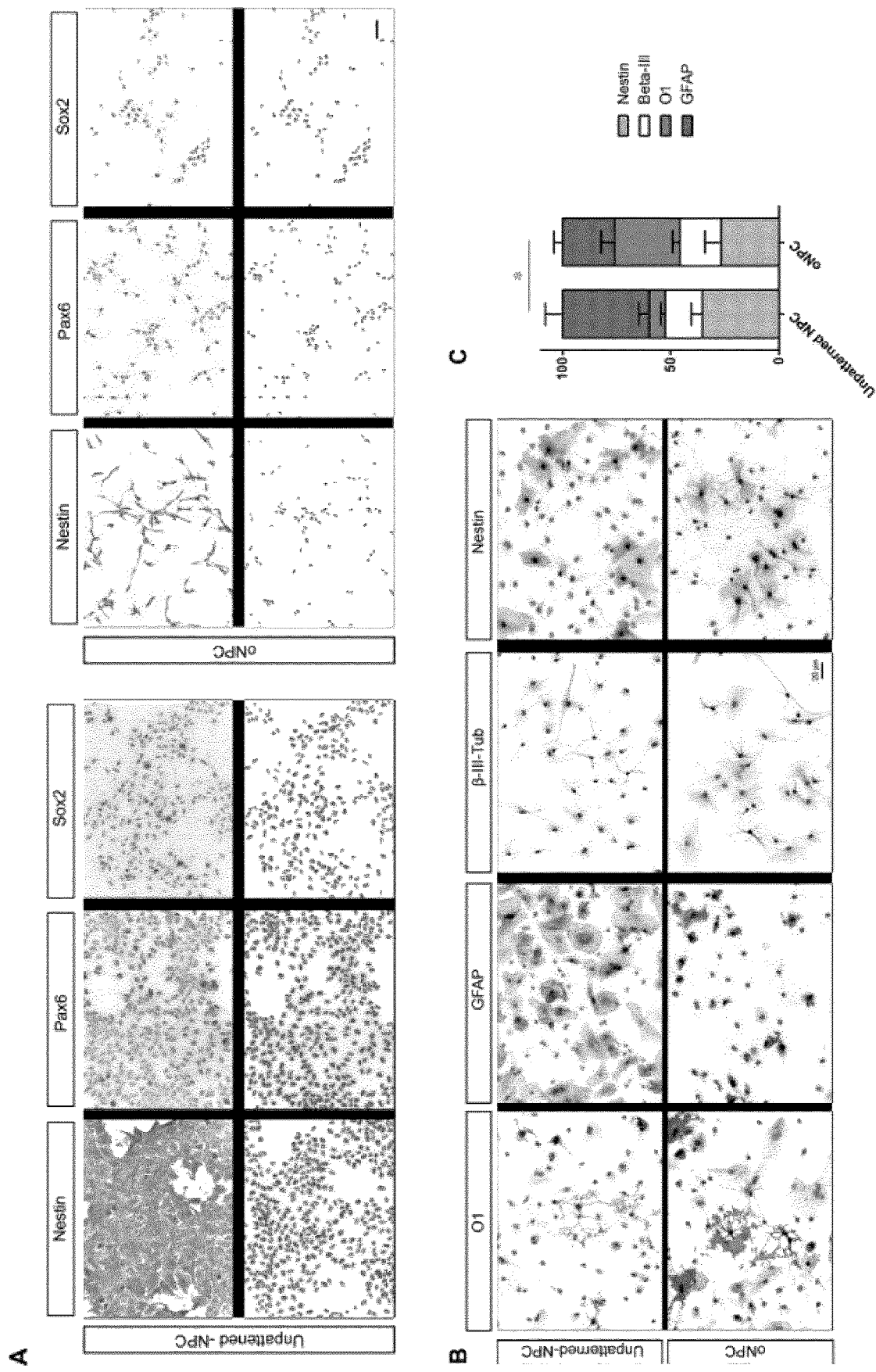
FIG. 11A-C In vitro differentiation profile of oNPCs. (A) Both unpatterned NPC and oNPCs demonstrated comparable expression of neural progenitor markers, Pax6, Sox2 and nestin. (B, C) Comparison of the differentiation profile of unpatterned NPC and oNPCs after removal of the growth factors EGF, FGF2 and addition of 0.1% FBS. These results and representative micrographs belong to drNPC derived cells. Results are presented as mean±SEM from three independent experiments (average of 10 random fields in each group). *p<0.05, **p<0.01, Student's t test. Scale bar: 20 µm.

The differentiation of unpatterned NPC and oNPC derivatives in vitro was examined. Both unpatterned NPCs and oNPCs demonstrated comparable expression of neural progenitor markers Pax6, Sox2 and nestin (FIG. 11A). These oNPCs could be expanded for up to three passages without losing their proliferation and differentiation capacity. After this stage, the proliferation rate of the cells slowed down and they eventually ceased proliferating at passage 5 to 6. At which point they morphologically appeared as flat, expanded cells. The cell cycle exit and initiation of differentiation was triggered by removal of the growth factors EGF, bFGF and addition of 0.1% FBS. After 10 days in differentiation conditions (e.g., removal of the growth factors EGF, bFGF and addition of 0.1% FBS for about 10 days) unpatterned hNPCs were characterized by marked process outgrowth, with an increase in the number of processes emanating from the cell body, and extensive branching of these processes. The morphological changes in NPCs were accompanied by the expression of structural markers characteristic of neuroglial differentiation: astrocytes (GFAP+; 40.1±7.9%), neurons (β-III tubulin+; 17.2±2.05%), and oligodendrocytes (O1+; 7.4.00±4.8%) (FIGS. 11B and C). oNPCs cultured in the same differentiation conditions for 10 days displayed a ramified morphology with an intricate lacework of processes that surrounded the cell body. Immunocytochemistry revealed the presence of neurons (βIII-tubulin+; 19.1±3.23%), but fewer astrocytes (GFAP+; 23.95±4.03%) and a significant increase in the numbers of oligodendrocytes (O1+; 30.23±6.22%) (FIG. 11C) demonstrated the multipotency of oNPC and their predisposition for generating oligodendrocytes.

Example 10

Figure 12:
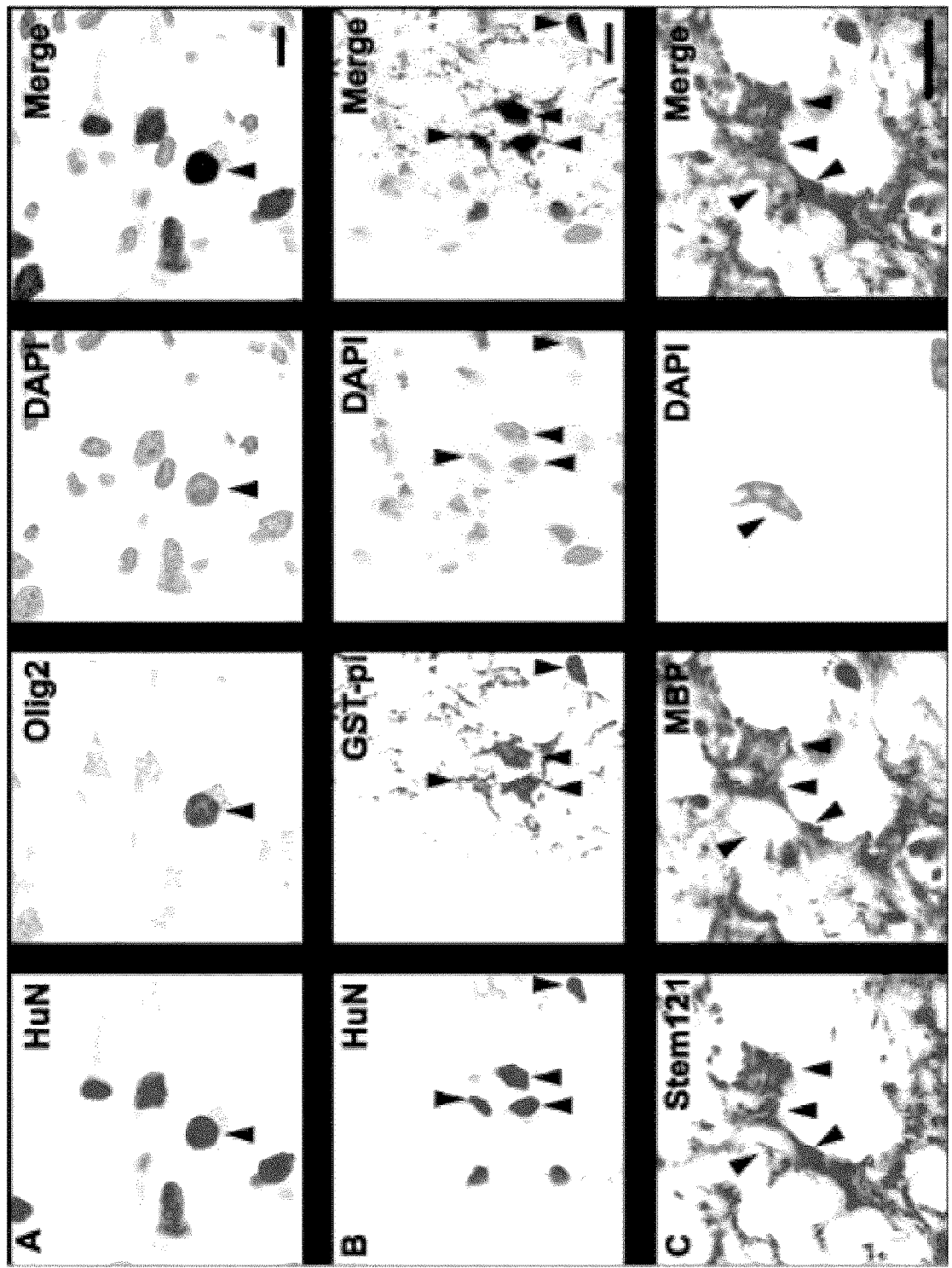
FIG. 12A-E oNPCs predominantly differentiated into oligo-lineage cells, and myelinated host axons. (A-D) Representative images of Olig2+/HuN+ immature (A) and GST-pi+/HuN+ mature (B) oligodendrocytes (arrowheads). Cytoplasm of the transplanted Stem121+ cells co-localized with MBP (C; arrowheads), and there were MBP+/Stem121+ mature oligodendrocytes myelinating host NF 200+ neuronal axons (D; arrowheads). These cells mainly existed in the white matter area of the spinal cord. (E-I) Representative images of immunoelectron microscopy in oNPCs (E-G), NPC (H) and vehicle groups (I). Grafted cells were detected by the black dots observed upon anti-Stem121 antibody staining. At higher magnifications in the oNPC group, remyelinated axons surrounded by transplanted cells were identified (F) and endogenous myelin from oligodendrocytes were preserved (G). Arrowheads and arrows indicate myelin derived from transplanted cells and endogenous cells, respectively. Scale bar: 10 µm in (A-D), 2 µm in (E, H, I), and 200 nm in (F, G).
Figure 12:
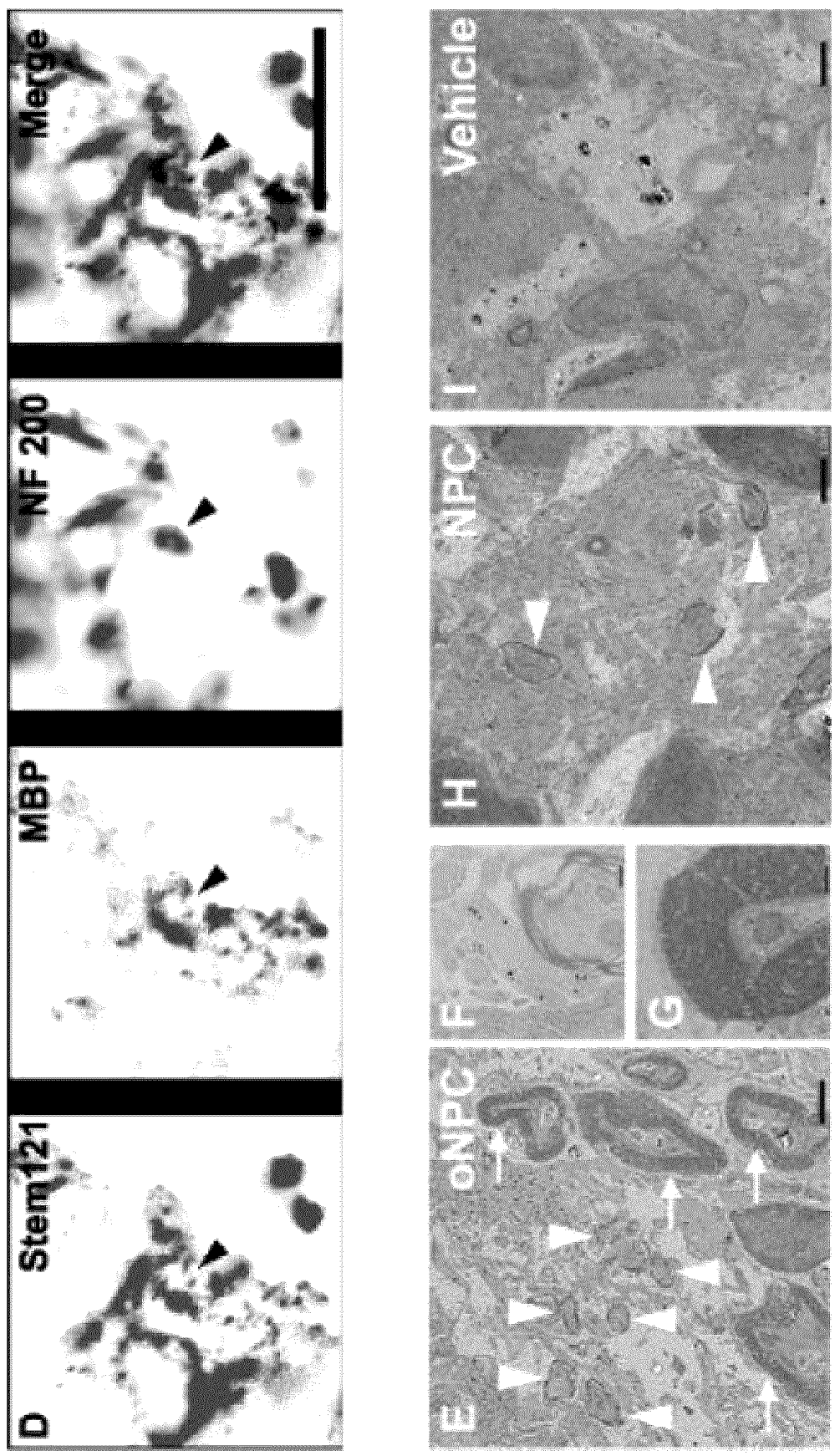

To analyze the oligodendrocyte-lineage cells differentiated from oNPCs, detailed immunohistochemistry was conducted with several oligodendrocyte markers. The transplanted oNPCs differentiated into Olig2+ immature and GST-pi+ mature oligodendrocytes (FIGS. 12A and B). Notably, they expressed MBP which are closely associated with host NF200+ axons (FIG. 12C-D), indicating the potential of transplanted oNPCs to remyelinate host axons in the injured spinal cord.

To evaluate the distribution of myelin after cell transplantation, electron microscopic examination was performed at the lesion epicenter. In the oNPC group, immature myelin sheaths derived from engrafted human cells (nanogold-labeled Stem121+) were frequently observed (FIGS. 12E and F). In addition, endogenous myelin from host oligodendrocytes was preserved (FIGS. 12E and G). The myelination by the control NPC group was not as robust as the oNPC group. The vehicle group showed only a few myelinated axons at the lesion site (FIG. 12I). Therefore, oNPCs generated myelinating oligodendrocytes following transplantation in vivo.

Figure 13:
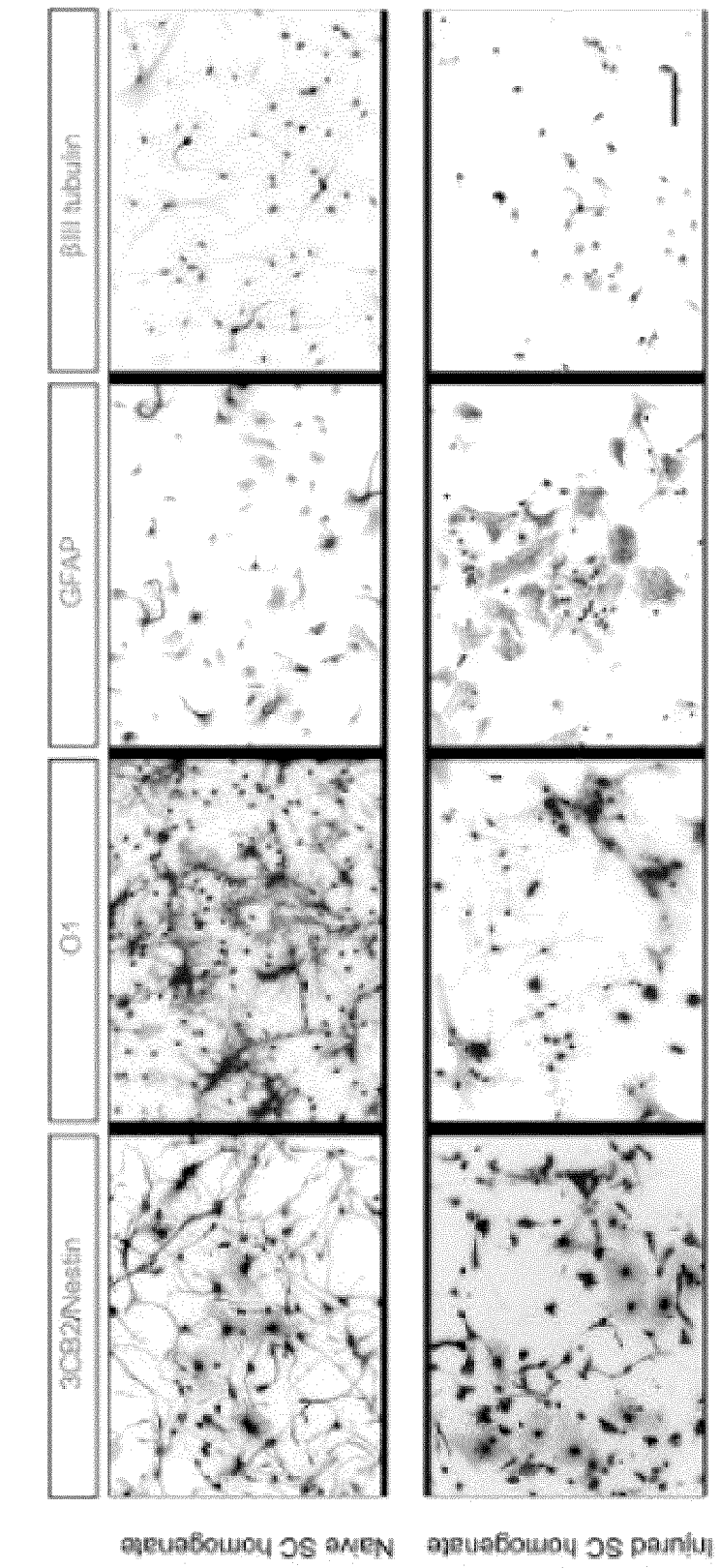
FIG. 13A-C in vitro oNPCs differentiation assay with or without CSPGs. (Chondroitin Sulfate ProteoGlycan). oNPCs cultured on dishes coated with spinal cord homogenates from uninjured (Naïve-h) or SCI-lesioned animals (SCI-h) for a week. (A) Cells were fixed and stained for the neural progenitor cell marker (Nestin), radial glial cell marker (3CB2; cytoplasmic projection stained), oligodendrocyte marker (O1), astrocyte marker (GFAP) or neuronal marker (βIII tubulin). (B) The percentage of cells positive for GFAP, O1, βIII tubulin or Nestin were quantified (n=3 biological replicates/group). (C) qRT-PCR analysis of the expression profile of neurogenic, astrocytogenic and oligodendrogenic transcription factors in oNPCs cultured on SCI-h relative to control-oNPCs cultured on Naïve-h with no treatment. Data represent the mean Log 2-fold change in gene expression relative to control cells (n=3 biological replicates/group). Values are expressed as the mean±SEM. *p<0.05. (Scale bar, 30 µm in A).
Figure 13:
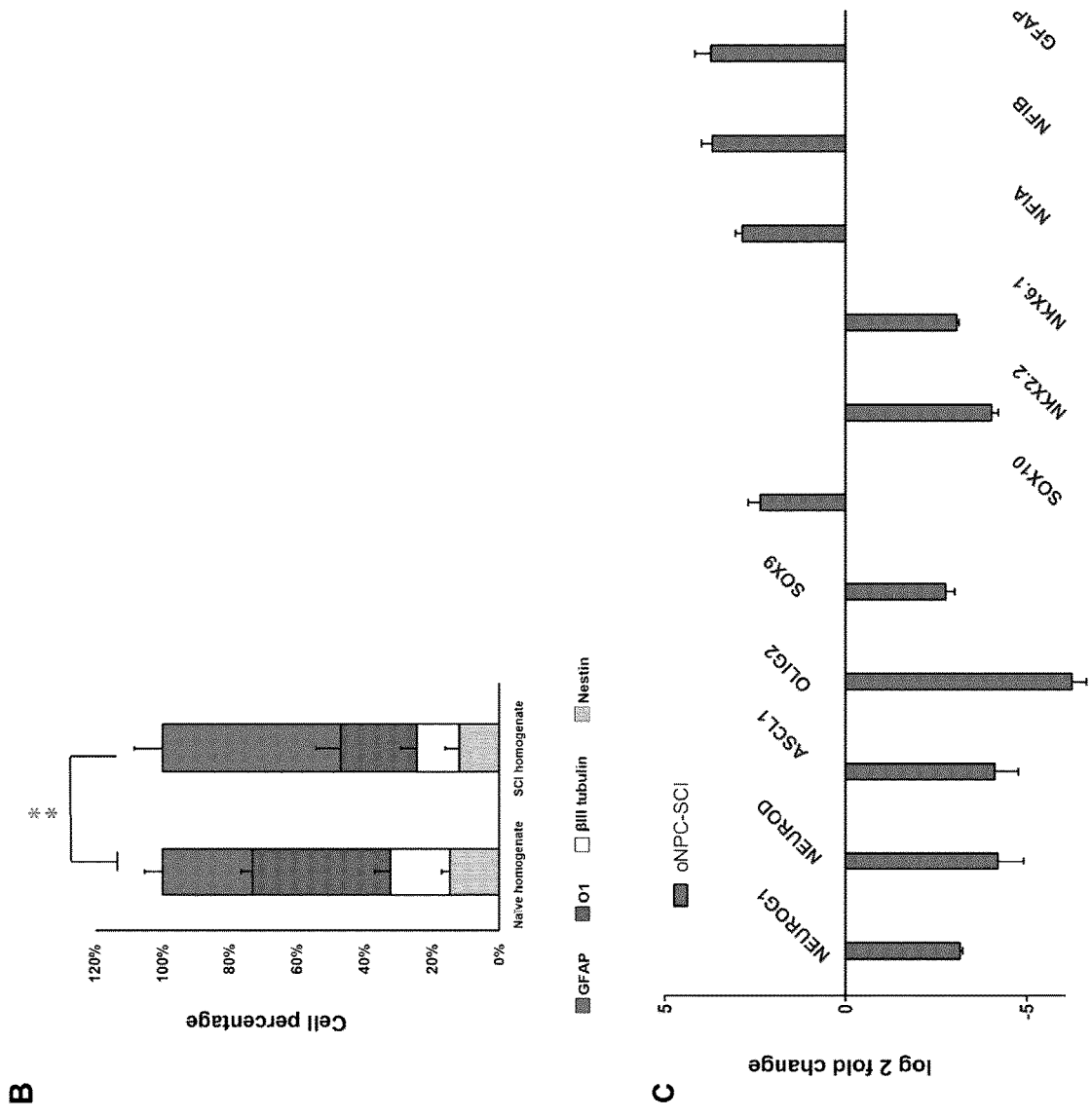

Example 11 oNPCs were cultured in the absence of FGF2/EGF on coverslips coated with 100 μg/ml homogenate from the injured (SCI-h) or naïve spinal cord (Naïve-h) for one week. The method attempts in vitro to mimic the factors which are present in naïve or injured spinal cord during the time of transplantation, the naïve homogenate should contain all (or most of) the factors which exist in spinal cord normally without injury, and injured homogenate should have most of the factors that are in microenvironment after injury. Withdrawal of FGF2/EGF for this period resulted in advancement of the majority of cells to radial glial cells expressing 3CB2, while around 15% of cells still remained in the neural progenitor stage, as evidenced by Nestin expression, after 1 week of treatment. Culturing oNPCs in SCI-h resulted in a significant increase in the number of glial fibrillary acidic protein (GFAP)+ cells (52.9±8.4%) as compared to cells cultured in Naïve-h (26.8±5.3%; p<0.01). A significant decrease in the number of cells expressing the oligodendrocyte marker O1 was observed when cultured with SCI-h (22.5±7.3%) as compared to cells cultured in Naïve-h (40.8±3.4%; p<0.01). However, no significant change in the number of β-tubulin isotype III (βIII tubulin)-positive neurons was observed in SCI-h cells (12.5±4.8%) as compared to cells treated with Naïve-h (17.5±4.6%) (FIGS. 13A and 4B). As shown here, the factors that are present in spinal cord microenvironment after injury, can change the fate of cells from oligodendrocytes to astrocytes but have no effect of the fate of neurons. When oNPCs are used, the fate alteration can be reduced resulting in more oligodendrocytes and fewer astrocytes in injured spinal cord microenvironment (SCI-h).

Furthermore, the expression of transcription factors (TFs) was influenced by SCI-h. For oNPCs cultured with SCI-h, the expression of pro-astrocytic TFs, NFIa and NFIb, was significantly upregulated compared to control cells cultured on Naïve-h. Conversely, the expression of pro-neuronal TFs, Ascl1, Atoh1 and Ngn1, and pro-oligodendrocytic TFs, Olig2, Nkx2.2, Nkx6.2, and Sox9, were significantly downregulated as compared to control cells cultured on Naïve-h (FIG. 13C).

Example 12

Improvement of Motor Function without Allodynia After oNPC Transplantation

Rats received cell transplantation 2 weeks (subacute phase of injury) or 8 weeks (Chronic) following SCI. Cells were dissociated into a single-cell suspension by using Accutase [or Trypsin, or papaein] at a concentration of $5 \times 10^4$ cells/μl to $20 \times 10^4$ cells/μl in neural expansion medium, and were transplanted (2 μl) bilaterally at 4 positions caudal and rostral to the lesion epicenter, bilateral to the midline. Injections sites were situated approximately 2 mm from the midline and entered 1 mm deep into the cord. Intraparenchymal cell transplantation requires slow injections and gradual needle withdrawal to ensure cells do not reflux out of the needle tract. When inserting the needle, the entire bevel should be below the pia mater to ensure injection into the cord. When removing the needle, additional time may be required if reflux is seen. This can be modified as required.

Figure 14:
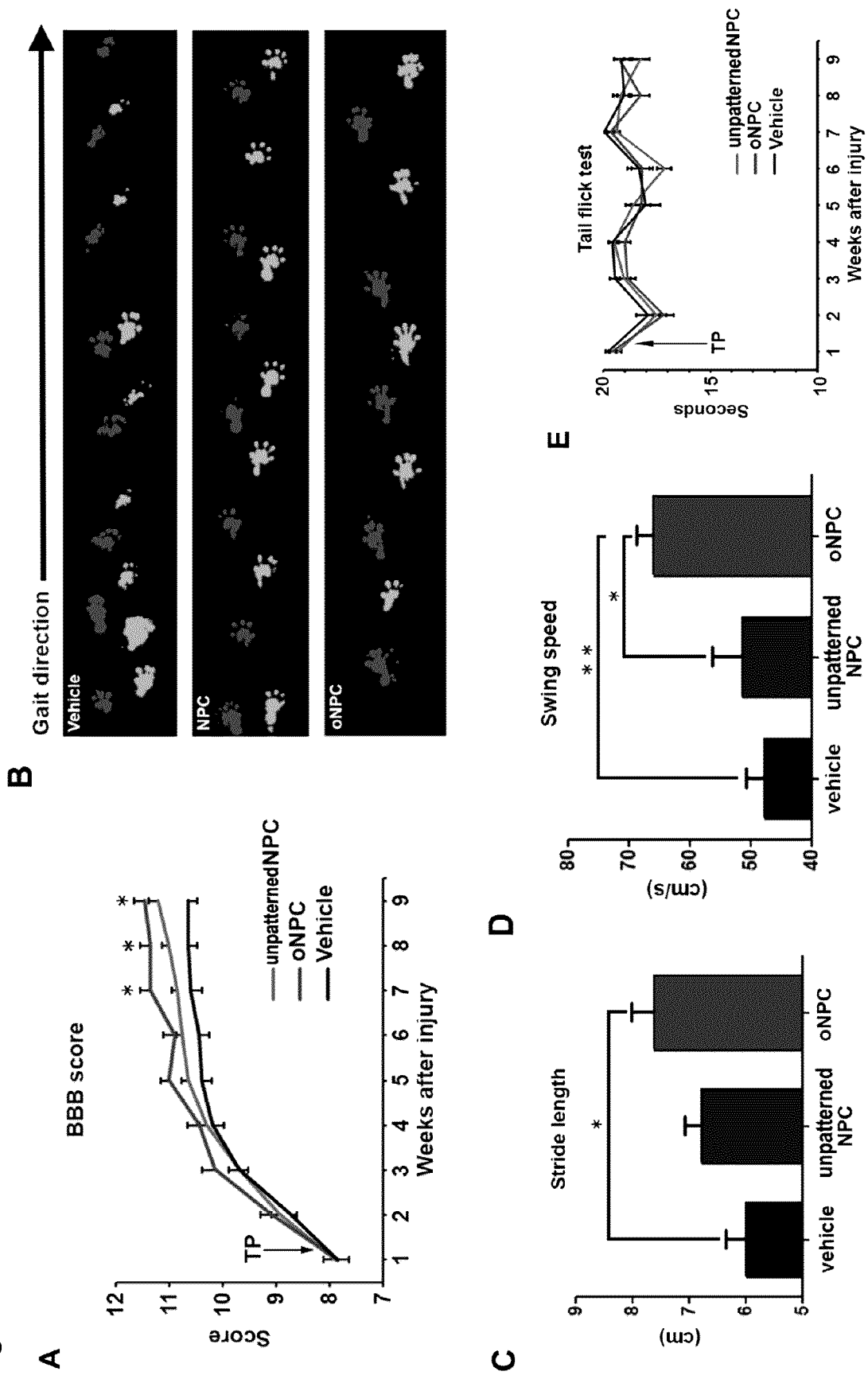
FIG. 14A-E Functional analysis following cell transplantation. (A) Time course of motor functional recovery of hindlimbs in BBB score. Rats with oNPCs transplantation showed significant recovery from 7 to 9 weeks after SCI. (B) Representative images of gait analysis with CatWalk system 9 weeks after SCI. Light and dark footprints indicate right and left hindlimbs, respectively. (C,D) Gait analysis with the CatWalk system. Note that there was significantly better recovery in stride length between the oNPC and vehicle groups, and swing speed in the oNPC group compared to the other groups. (E) Evaluation of thermal allodynia in the tail-flick test. In each test, 10 rats per each group were examined. *p<0.05; **p<0.01.
Figure 15:
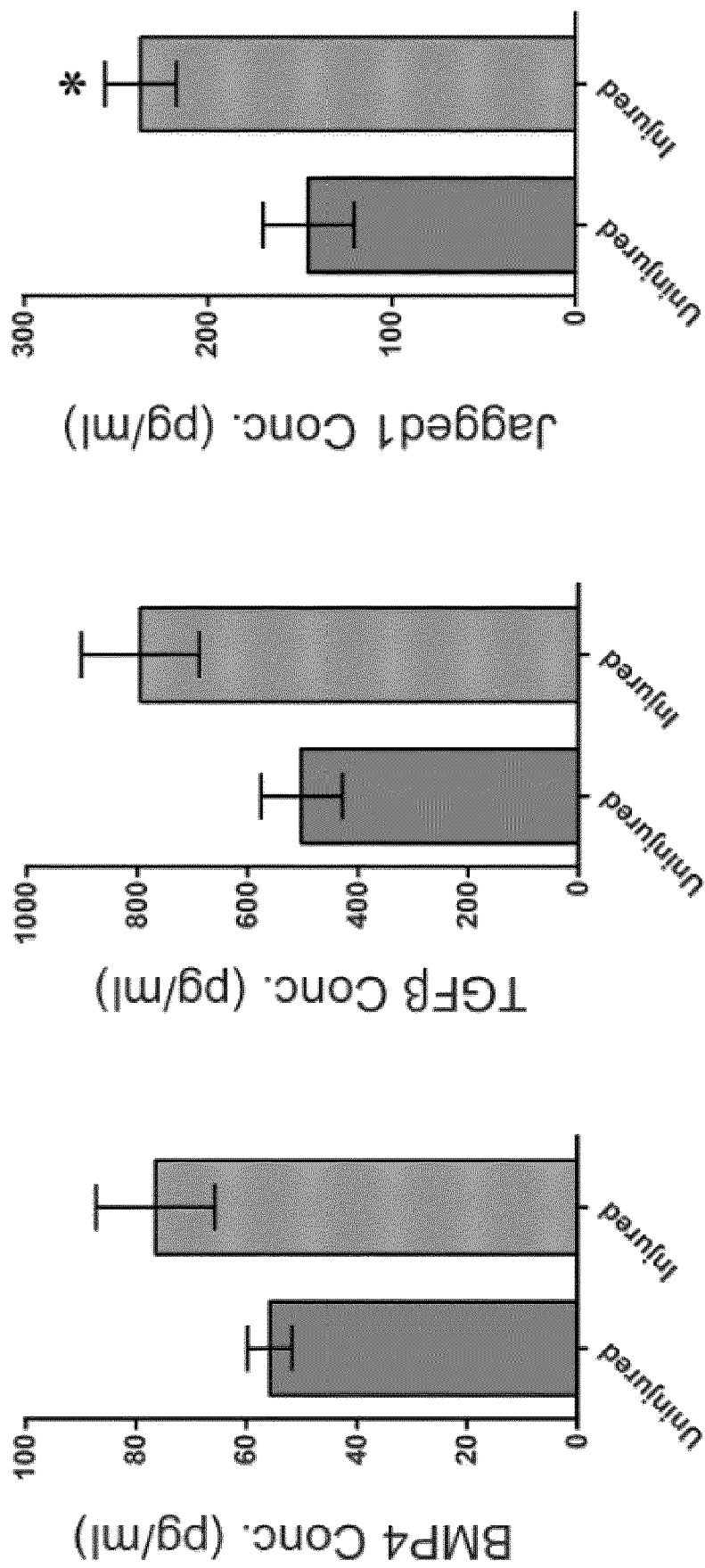
FIG. 15. Levels of BMP4, TGF-β and Jagged1 detected in the cervical spinal cord at two weeks post-injury.

Locomotor coordination and trunk stability using the BBB open-field locomotion scale was evaluated. BBB scores showed significantly improved functional recovery after SCI in the oNPC group compared to the vehicle group (week 7-9; p<0.05) (FIG. 14A). Further, a gait analysis using the CatWalk Digital Gait Analysis system (Noldus Inc.; FIG. 14B) was conducted. Gait analysis revealed that oNPC transplanted rats had significantly better recovery in terms of stride length and swing speed relative to the vehicle and control unpatterned-NPC group (FIGS. 14C and D). To determine whether sensory impairments occurred following cell transplantation, the tail-flick test was used to measure thermal allodynia. Notably, no significant difference was found between groups, suggesting that the transplanted cells did not contribute to post-injury sensory dysfunction (FIG. 14E).

Example 13 oNPCs were differentiated as described in Example 11. The concentration of BMP4, TGFβ and Jagged1 was compared between injured spinal cord homogenate (SCI-h) and (naïve spinal cord homogenate) Naïve-h (1 mg/ml total protein) using ELISA.

An increase in the expression of BMP4, TGF-β and Jagged1 was detected in the cervical spinal cord at two weeks post-injury, the timepoint which we transplant cells into the spinal cord.

Example 14

Culture Media Formulation used in Examples:

| | |
|---|---|
| Neural induction medium (NIM) | DMEM/F12 medium, supplemented with sodium pyruvate, glutamax, 1% penicillin, streptomycin solution, N2, B27 without vitamin A, Non-essential amino acids, FGF2, EGF (20 ng/mL), heparin, TGFβ-inhibitor (SB 431542), BMP-inhibitor (LDN 193189 or Noggin) |
| NPC expansion medium (NEM) | DMEM/F12 medium supplemented with sodium pyruvate, Glutamax, 1% penicillin, streptomycin solution, N2, B27 without vitamin A, 1% MEM (containing essential amino acids), FGF2, EGF and heparin. |

CITATIONS FOR REFERENCES REFERRED TO IN THE SPECIFICATION

Ahuja, C. S., & Fehlings, M. (2016). Concise review: Bridging the gap: Novel neuroregenerative and neuroprotective strategies in spinal cord injury. Stem Cells Translational Medicine, 5, 914-924. doi: 10.5966/sctm.2015-0381.

Ahuja, C., Martin, A., & Fehlings, M. (2016). Recent advances in managing patients with spinal cord injury secondary to trauma. F1000 Faculty Reviews, in press.

Barres, B. A., Lazar, M. A., & Raff, M. C. (1994). A novel role for thyroid hormone, glucocorticoids and retinoic acid in timing oligodendrocyte development. Development, 120, 1097-1108.

Chambers, S. M., Fasano, C. A., Papapetrou, E. P., Tomishima, M., Sadelain, M., & Studer, L. (2009). Highly efficient neural conversion of human ES and iPS cells by dual inhibition of SMAD signaling. Nature Biotechnology, 27, 275-280. doi: 10.1038/nbt.1529.

Chang D. J., Oh S. H., Lee N., Choi C., Jeon I., Kim H. S., Shin D. A., Lee S. E., Kim D., Song J. (2013). Contralaterally transplanted human embryonic stem cell-derived neural precursor cells (ENStem-A) migrate and improve brain functions in strokedamaged rats. Experimental & Molecular Medicine, 45, e53. doi: 10.1038/emm.2013.93.

Fehlings, M. G., & Tator, C. H. (1995). The relationships among the severity of spinal cord injury, residual neurological function, axon counts, and counts of retrogradely labeled neurons after experimental spinal cord injury. Experimental Neurology, 132, 220-228. doi: 10.1016/0014-4886(95)90027-6.

Ghasemi-Dehkordi P, Allahbakhshian-Farsani M, Abdian N, Mirzaeian A, Saffari-Chaleshtori J, Heybati F, Mardani G, Karimi-Taghanaki A, Doosti A, Jami M S, Abolhasani M, Hashemzadeh-Chaleshtori M. (2015). Comparison between the cultures of human induced pluripotent stem cells (hiPSCs) on feeder-and serumfree system (Matrigel matrix), MEF and HDF feeder cell lines. Journal of Cell Communication and Signaling, 9, 233-246. doi: 10.1007/s12079-015-0289-3.

Hawryluk G W, Spano S, Chew D, Wang S, Erwin M, Chamankhah M, Forgione N, Fehlings M G. (2014). An examination of the mechanisms by which neural precursors augment recovery following spinal cord injury: A key role for remyelination. Cell Transplant, 23, 365-380. doi: 10.3727/096368912X662408.

Khazaei, M., Ahuja, C. S., & Fehlings, M. G. (2017). Induced pluripotent stem cells for traumatic spinal cord injury. Frontiers in Cell and Developmental Biology, 4, 152 doi: 10.3389/fcell.2016.00152.

Le Dreau, G., & Marti, E. (2012). Dorsal-ventral patterning of the neural tube: A tale of three signals. Developmental Neurobiology, 72, 1471-1481. doi: 10.1002/dneu.22015.

Lu, Q. R., Sun, T., Zhu, Z., Ma, N., Garcia, M., Stiles, C. D., & Rowitch, D. H. (2002). Common developmental requirement for olig function indicates a motor neuron/oligodendrocyte connection. Cell, 109, 75-86. doi: 10.1016/S0092-8674(02)00678-5.

Papastefanaki, F., & Matsas, R. (2015). From demyelination to remyelination: The road toward therapies for spinal cord injury. Glia, 63, 1101-1125. doi: 10.1002/glia.22809.

Plaisted W C, Zavala A, Hingco E, Tran H, Coleman R, Lane T E, Loring J F, Walsh C M. (2016). Remyelination Is correlated with regulatory T cell induction following human embryoid body-derived neural precursor cell transplantation in a viral model of multiple sclerosis. PLoS One, 11, e0157620. doi: 10.1371/journal.pone.0157620.

Skop, N. B., Calderon, F., Cho, C. H., Gandhi, C. D., & Levison, S. W. (2016). Optimizing a multifunctional microsphere scaffold to improve neural precursor cell transplantation for traumatic brain injury repair. Journal of Tissue Engineering and Regenerative Medicine, 10, E419-E432. doi: 10.1002/term.1832.

Takahashi, K., & Yamanaka, S. (2006). Induction of pluripotent stem cells from mouse embryonic and adult fibroblast cultures by defined factors. Cell, 126, 663-676. doi: 10.1016/j.cell.2006.07.024.

Wang S, Bates J, Li X, Schanz S, Chandler-Militello D, Levine C, Maherali N, Studer L, Hochedlinger K, Windrem M, Goldman S A. (2013). Human iPSC-derived oligodendrocyte progenitor cells can myelinate and rescue a mouse model of congenital hypomyelination. Cell Stem Cell, 12, 252-264. doi: 10.1016/j.stem.2012.12.002.

Wilson, L., & Maden, M. (2005). The mechanisms of dorsoventral patterning in the vertebrate neural tube. Developmental Biology, 282, 1-13. doi: 10.1016/j.ydbio.2005.02.027.

Zhou, Q., Choi, G., & Anderson, D. J. (2001). The bHLH Transcription factor Olig2 promotes oligodendrocyte differentiation in collaboration with Nkx2.2. Neuron, 31, 791-807. doi: 10.1016/50896-6273(01)00414-7.

Zweckberger, K., Ahuja, C. S., Liu, Y., Wang, J., & Fehlings, M. G. (2016). Self-assembling peptides optimize the post-traumatic milieu and synergistically enhance the effects of neural stem cell therapy after cervical spinal cord injury. Acta Biomaterialia, 42, 77-89. doi: 10.1016/j.actbio.2016.06.016.

The invention claimed is:

1. A method of producing oligodendrogenic neural progenitor cells (o-NPCs), the method comprising:
 a) obtaining iPSCs cultured for at least about 2 days in vessels comprising a gelatinous matrix with an induced pluripotent cell media/embryonic cell media supplemented with a ROCK inhibitor and culturing the iPSCs:
  i. in NIM supplemented with leukemia inhibitory factor (LIF), FGF agonist, B27 supplement lacking vitamin A, N2 supplement, TGFb inhibitor, BMP inhibitor for about 7 days; and
  ii. in NIM supplemented with EGFR agonist, FGFR agonist, B27 supplement lacking vitamin A and N2 supplement, wherein the iPSCs are cultured in vessels coated with a gelatinous matrix comprising poly-L-lysine/laminin for about 1 to 2 days to produce columnar cells in the form of rosettes expressing Pax 6;
b) culturing the columnar cells in the form of rosettes from step ii. in NEM comprising EGFR agonist, FGFR agonist, B27 lacking vitamin A, and N2 supplement for about 4 days, wherein the columnar cells are cultured in vessels coated with a gelatinous matrix comprising poly-L-lysine/laminin, to produce unpatterned NPCs;
c) culturing the unpatterned NPCs from step b) for about 6 days in NEM comprising retinoic acid, N2 supplement, B27 supplement, EGFR agonist and a Shh agonist to produce caudalized NPCs;
d) culturing the caudalized NPCs from step c):
 i. in NEM comprising EGFR agonist, N2 supplement, B27 supplement, retinoic acid and Shh agonist for about 3 to about 6 days; and
 ii. in NEM comprising FGFR agonist, N2 supplement, B27 supplement and a Shh agonist for about 3 days to obtain ventralized NPCs;
e) culturing the ventralized NPCs for about 12 to about 16 days in NEM comprising i) PDGFR agonist for the about 12 to about 16 days; ii) B27 and N1 supplements for the preliminary about 12 days; and iii) thyroxine or a thyroxine analogue for the latter about 7 to about 9 days to produce o-NPCs.

2. The method of claim 1 wherein the NEM of step e) is also supplemented with an FGFR agonist.

3. The method of claim 1, wherein the o-NPCs produced are biased to differentiation towards oligodendrocytes.

4. The method of claim 1, wherein the Shh agonist is selected from purmorphamine, smoothened agonist (SAG) and recombinant Shh polypeptide, Desert hedge hog (Dhh), mammalian Indian hedge hog (Ihh) and/or activates Smoothened (SMO).

5. The method of claim 1 wherein the EGFR agonist is EGF and/or the FGFR agonist is FGF2.

6. The method of claim 1, wherein one or more of the culturing steps are cultured using a monolayer system.

7. The method of claim 1, wherein the NIM of step a) i) is further supplemented with an AMP-activated protein kinase (AMPK) inhibitor.

8. The method of claim 1, wherein the iPSCs are hiPSCs and/or wherein the iPSCs are a hiPSC cell line.

9. The method of claim 1, wherein the thyroxine analogue is selected from thyroxine, levothyroxine sodium hydrate and triiodothyronine/thyroid hormone 3 (T3) and/or wherein the PDGFR agonist is PDGF.

10. The method of claim 1, further comprising differentiating the oNPCs to obtain a differentiated population enriched for oligodendrocyte lineage cells.

11. The method of claim 10, wherein the step of differentiating the oNPCs comprises culturing oNPCs in NEM lacking FGFR agonist/EGFR agonist to produce a radial glial cell 3CB2 enriched population of cells.

12. The method of claim 10, wherein the oligodendrocyte lineage cells are Olig2+ immature and GST-pi+ mature oligodendrocytes.

13. The method of claim 3, wherein the oNPCs produce at least 30% oligodendrocytes when differentiated.

14. The method of claim 2, wherein the FGFR agonist is FGF2 or FGF8.

15. The method of claim 11, wherein the oNPCs are differentiated on vessels coated with spinal cord homogenate.

16. The method of claim 15, wherein the spinal cord homogenate is injured or naïve spinal cord homogenate.

17. The method of claim 1, wherein the BMP inhibitor is Noggin.

18. The method of claim 9, wherein the PDGF is PDGF-AA, PDGF-AB, PDGF-BB, and/or PDGF-CC.

19. The method of claim 7, wherein the AMPK inhibitor is compound C or Dorsomorphin.

20. The method of claim 1, wherein the NIM of step a) i) is further supplemented with a GSK3β inhibitor.

* * * * *